(12) United States Patent
Nelson et al.

(10) Patent No.: US 8,066,639 B2
(45) Date of Patent: Nov. 29, 2011

(54) GLUCOSE MEASURING DEVICE FOR USE IN PERSONAL AREA NETWORK

(75) Inventors: Charles L. Nelson, Santa Rosa, CA (US); Mark K. Sloan, Hayward, CA (US); Robert Y. Jin, Lafayette, CA (US); Feng Jiang, Union City, CA (US); Jen-Chyun Chen, San Jose, CA (US); Arthur Eugene Anderson, III, Sunnyvale, CA (US); Charles T. Liamos, Pleasanton, CA (US); Douglas C. Limbach, Los Altos, CA (US)

(73) Assignee: Abbott Diabetes Care Inc., Alameda, CA (US)

( * ) Notice: Subject to any disclaimer, the term of this patent is extended or adjusted under 35 U.S.C. 154(b) by 0 days.

(21) Appl. No.: 10/861,625

(22) Filed: Jun. 4, 2004

(65) Prior Publication Data

US 2005/0003470 A1    Jan. 6, 2005

Related U.S. Application Data

(60) Provisional application No. 60/477,730, filed on Jun. 10, 2003.

(51) Int. Cl.
*A61B 5/00* (2006.01)
*G05D 1/00* (2006.01)

(52) U.S. Cl. .............. 600/301; 600/300; 701/1; 436/95

(58) Field of Classification Search .......... 600/300–301, 600/309, 316, 323, 347, 361, 365, 549, 345; 128/897, 903–905, 920–925; 705/1–4; 604/93.01, 604/65–67; 340/573.1; 220/834
See application file for complete search history.

(56) References Cited

U.S. PATENT DOCUMENTS

| | | | |
|---|---|---|---|
| 2,755,036 | A | 7/1956 | Mikko |
| 3,260,656 | A | 7/1966 | Ross, Jr. |
| 3,304,413 | A | 2/1967 | Lehmann et al. |
| 3,581,062 | A | 5/1971 | Aston |
| 3,651,318 | A | 3/1972 | Czekajewski |

(Continued)

FOREIGN PATENT DOCUMENTS

DE    42 34 553 C2    1/1995

(Continued)

OTHER PUBLICATIONS

Abruna, H. D., et al., "Rectifying Interfaces Using Two-Layer Films of Electrochemically Polymerized Vinylpyridine and Vinylbipyridine Complexes of Ruthenium and Iron on Electrodes", *Journal of the American Chemical Society*, vol. 103, No. 1, 1981, pp. 1-5.

(Continued)

*Primary Examiner* — Sam Yao
*Assistant Examiner* — Bobby Soriano
(74) *Attorney, Agent, or Firm* — Jackson & Co., LLP

(57) ABSTRACT

A glucose measuring system includes a glucose meter that incorporates wireless communication capabilities. The meter can advantageously be a low cost meter by eliminating expensive components, such as the display. The user nevertheless is able to retrieve and view his or her glucose values by referring to displays within the glucose measuring local area network. Feedback via these displays can advantageously be used by the diabetic to create a higher level of confidence and safety.

41 Claims, 5 Drawing Sheets

U.S. PATENT DOCUMENTS

| | | |
|---|---|---|
| 3,653,841 A | 4/1972 | Klein |
| 3,698,386 A | 10/1972 | Fried |
| 3,719,564 A | 3/1973 | Lilly, Jr. et al. |
| 3,768,014 A | 10/1973 | Smith et al. |
| 3,776,832 A | 12/1973 | Oswin et al. |
| 3,837,339 A | 9/1974 | Aisenberg et al. |
| 3,919,051 A | 11/1975 | Koch et al. |
| 3,926,760 A | 12/1975 | Allen et al. |
| 3,949,388 A | 4/1976 | Fuller |
| 3,972,320 A | 8/1976 | Kalman |
| 3,979,274 A | 9/1976 | Newman |
| 4,003,379 A | 1/1977 | Ellinwood, Jr. |
| 4,008,717 A | 2/1977 | Kowarski |
| 4,016,866 A | 4/1977 | Lawton |
| 4,036,749 A | 7/1977 | Anderson |
| 4,055,175 A | 10/1977 | Clemens et al. |
| 4,059,406 A | 11/1977 | Fleet |
| 4,076,596 A | 2/1978 | Connery et al. |
| 4,098,574 A | 7/1978 | Dappen |
| 4,100,048 A | 7/1978 | Pompei et al. |
| 4,129,128 A | 12/1978 | McFarlane |
| 4,151,845 A | 5/1979 | Clemens |
| 4,154,231 A | 5/1979 | Russell |
| 4,168,205 A | 9/1979 | Danniger et al. |
| 4,172,770 A | 10/1979 | Semersky et al. |
| 4,178,916 A | 12/1979 | McNamara |
| 4,206,755 A | 6/1980 | Klein |
| 4,224,125 A | 9/1980 | Nakamura et al. |
| 4,240,438 A | 12/1980 | Updike et al. |
| 4,240,889 A | 12/1980 | Yoda et al. |
| 4,245,634 A | 1/1981 | Albisser et al. |
| 4,247,297 A | 1/1981 | Berti et al. |
| 4,271,449 A | 6/1981 | Grogan |
| 4,318,784 A | 3/1982 | Higgins et al. |
| 4,331,869 A | 5/1982 | Rollo |
| 4,340,458 A | 7/1982 | Lerner et al. |
| 4,344,438 A | 8/1982 | Schultz |
| 4,349,728 A | 9/1982 | Phillips et al. |
| 4,352,960 A | 10/1982 | Dormer et al. |
| 4,356,074 A | 10/1982 | Johnson |
| 4,365,637 A | 12/1982 | Johnson |
| 4,366,033 A | 12/1982 | Richter et al. |
| 4,375,399 A | 3/1983 | Havas et al. |
| 4,384,586 A | 5/1983 | Christiansen |
| 4,390,621 A | 6/1983 | Bauer |
| 4,392,933 A | 7/1983 | Nakamura et al. |
| 4,401,122 A | 8/1983 | Clark, Jr. |
| 4,404,066 A | 9/1983 | Johnson |
| 4,407,959 A | 10/1983 | Tsuji et al. |
| 4,417,588 A | 11/1983 | Houghton et al. |
| 4,418,148 A | 11/1983 | Oberhardt |
| 4,420,564 A | 12/1983 | Tsuji et al. |
| 4,425,920 A | 1/1984 | Bourland et al. |
| 4,427,004 A | 1/1984 | Miller et al. |
| 4,427,770 A | 1/1984 | Chen et al. |
| 4,431,004 A | 2/1984 | Bessman et al. |
| 4,436,094 A | 3/1984 | Cerami |
| 4,440,175 A | 4/1984 | Wilkins |
| 4,441,968 A | 4/1984 | Emmer et al. |
| 4,444,892 A | 4/1984 | Malmros |
| 4,450,842 A | 5/1984 | Zick et al. |
| 4,458,686 A | 7/1984 | Clark, Jr. |
| 4,461,691 A | 7/1984 | Frank |
| 4,467,811 A | 8/1984 | Clark, Jr. |
| 4,469,110 A | 9/1984 | Slama |
| 4,477,314 A | 10/1984 | Richter et al. |
| 4,478,976 A | 10/1984 | Goertz et al. |
| 4,483,924 A | 11/1984 | Tsuji et al. |
| 4,484,987 A | 11/1984 | Gough |
| 4,494,950 A | 1/1985 | Fischell |
| 4,509,531 A | 4/1985 | Ward |
| 4,512,348 A | 4/1985 | Uchigaki et al. |
| 4,522,690 A | 6/1985 | Venkatsetty |
| 4,524,114 A | 6/1985 | Samuels et al. |
| 4,526,661 A | 7/1985 | Steckhan et al. |
| 4,527,240 A | 7/1985 | Kvitash |
| 4,534,356 A | 8/1985 | Papadakis |
| 4,538,616 A | 9/1985 | Rogoff |
| 4,543,955 A | 10/1985 | Schroeppel |
| 4,545,382 A | 10/1985 | Higgins et al. |
| 4,552,840 A | 11/1985 | Riffer |
| 4,560,534 A | 12/1985 | Kung et al. |
| 4,569,589 A | 2/1986 | Neufeld |
| 4,571,292 A | 2/1986 | Liu et al. |
| 4,573,994 A | 3/1986 | Fischell et al. |
| 4,581,336 A | 4/1986 | Malloy et al. |
| 4,595,011 A | 6/1986 | Phillips |
| 4,595,479 A | 6/1986 | Kimura et al. |
| 4,601,707 A | 7/1986 | Albisser et al. |
| 4,619,754 A | 10/1986 | Niki et al. |
| 4,619,793 A | 10/1986 | Lee |
| 4,627,445 A | 12/1986 | Garcia et al. |
| 4,627,908 A | 12/1986 | Miller |
| 4,633,878 A | 1/1987 | Bombardien |
| 4,633,881 A | 1/1987 | Moore et al. |
| 4,637,403 A | 1/1987 | Garcia et al. |
| 4,648,408 A | 3/1987 | Hutcheson et al. |
| 4,650,547 A | 3/1987 | Gough |
| 4,653,513 A | 3/1987 | Dombrowski |
| 4,654,197 A | 3/1987 | Lilja et al. |
| 4,655,880 A | 4/1987 | Liu |
| 4,655,885 A | 4/1987 | Hill et al. |
| 4,658,463 A | 4/1987 | Sugita et al. |
| 4,671,288 A | 6/1987 | Gough |
| 4,674,652 A | 6/1987 | Aten et al. |
| 4,679,562 A | 7/1987 | Luksha |
| 4,680,268 A | 7/1987 | Clark, Jr. |
| 4,682,602 A | 7/1987 | Prohaska |
| 4,684,537 A | 8/1987 | Graetzel et al. |
| 4,685,463 A | 8/1987 | Williams |
| 4,685,903 A | 8/1987 | Cable et al. |
| 4,686,624 A | 8/1987 | Blum et al. |
| 4,703,756 A | 11/1987 | Gough et al. |
| 4,711,245 A | 12/1987 | Higgins et al. |
| 4,717,673 A | 1/1988 | Wrighton et al. |
| 4,721,601 A | 1/1988 | Wrighton et al. |
| 4,721,677 A | 1/1988 | Clark, Jr. |
| 4,726,378 A | 2/1988 | Kaplan |
| 4,726,716 A | 2/1988 | McGuire |
| 4,731,726 A | 3/1988 | Allen, III |
| 4,749,985 A | 6/1988 | Corsberg |
| 4,750,496 A | 6/1988 | Reinhardt et al. |
| 4,757,022 A | 7/1988 | Shults et al. |
| 4,758,323 A | 7/1988 | Davis et al. |
| 4,759,371 A | 7/1988 | Franetzki |
| 4,759,828 A | 7/1988 | Young et al. |
| 4,764,416 A | 8/1988 | Ueyama et al. |
| 4,776,944 A | 10/1988 | Janata et al. |
| 4,777,953 A | 10/1988 | Ash et al. |
| 4,779,618 A | 10/1988 | Mund et al. |
| 4,781,798 A | 11/1988 | Gough |
| 4,784,736 A | 11/1988 | Lonsdale et al. |
| 4,795,707 A | 1/1989 | Niiyama et al. |
| 4,796,634 A | 1/1989 | Huntsman et al. |
| 4,803,625 A | 2/1989 | Fu et al. |
| 4,805,624 A | 2/1989 | Yao et al. |
| 4,813,424 A | 3/1989 | Wilkins |
| 4,815,469 A | 3/1989 | Cohen et al. |
| 4,820,399 A | 4/1989 | Senda et al. |
| 4,822,337 A | 4/1989 | Newhouse et al. |
| 4,830,959 A | 5/1989 | McNeil et al. |
| 4,832,797 A | 5/1989 | Vadgama et al. |
| 4,835,372 A | 5/1989 | Gombrich et al. |
| 4,837,049 A | 6/1989 | Byers et al. |
| 4,840,893 A | 6/1989 | Hill et al. |
| RE32,974 E | 7/1989 | Porat et al. |
| 4,844,076 A | 7/1989 | Lesho et al. |
| 4,845,035 A | 7/1989 | Fanta et al. |
| 4,848,351 A | 7/1989 | Finch |
| 4,854,322 A | 8/1989 | Ash et al. |
| 4,856,340 A | 8/1989 | Garrison |
| 4,857,713 A | 8/1989 | Brown |
| 4,858,617 A | 8/1989 | Sanders |
| 4,870,561 A | 9/1989 | Love et al. |
| 4,871,351 A | 10/1989 | Feingold |
| 4,871,440 A | 10/1989 | Nagata et al. |
| 4,874,499 A | 10/1989 | Smith et al. |

| | | | | | |
|---|---|---|---|---|---|
| 4,874,500 A | 10/1989 | Madou et al. | 5,114,678 A | 5/1992 | Crawford et al. |
| 4,890,620 A | 1/1990 | Gough | 5,120,420 A | 6/1992 | Nankai et al. |
| 4,890,621 A | 1/1990 | Hakky | 5,120,421 A | 6/1992 | Glass et al. |
| 4,894,137 A | 1/1990 | Takizawa et al. | 5,122,925 A | 6/1992 | Inpyn |
| 4,897,162 A | 1/1990 | Lewandowski et al. | 5,126,034 A | 6/1992 | Carter et al. |
| 4,897,173 A | 1/1990 | Nankai et al. | 5,126,247 A | 6/1992 | Palmer et al. |
| 4,899,839 A | 2/1990 | Dessertine et al. | 5,130,009 A | 7/1992 | Marsoner et al. |
| 4,909,908 A | 3/1990 | Ross et al. | 5,133,856 A | 7/1992 | Yamaguchi et al. |
| 4,911,794 A | 3/1990 | Parce et al. | 5,134,391 A | 7/1992 | Okada |
| 4,917,800 A | 4/1990 | Lonsdale et al. | 5,135,003 A | 8/1992 | Souma |
| 4,919,141 A | 4/1990 | Zier et al. | 5,139,023 A | 8/1992 | Stanley et al. |
| 4,919,767 A | 4/1990 | Vadgama et al. | 5,140,393 A | 8/1992 | Hijikihigawa et al. |
| 4,920,969 A | 5/1990 | Suzuki | 5,141,868 A | 8/1992 | Shanks et al. |
| 4,920,977 A | 5/1990 | Haynes | 5,161,532 A | 11/1992 | Joseph |
| 4,923,586 A | 5/1990 | Katayama et al. | 5,165,407 A | 11/1992 | Wilson et al. |
| 4,925,268 A | 5/1990 | Iyer et al. | 5,168,046 A | 12/1992 | Hamamoto et al. |
| 4,927,516 A | 5/1990 | Yamaguchi et al. | 5,174,291 A | 12/1992 | Schoonen et al. |
| 4,931,795 A | 6/1990 | Gord | 5,176,644 A | 1/1993 | Srisathapat et al. |
| 4,934,369 A | 6/1990 | Maxwell | 5,176,662 A | 1/1993 | Bartholomew et al. |
| 4,935,105 A | 6/1990 | Churchouse | 5,182,707 A | 1/1993 | Cooper et al. |
| 4,935,345 A | 6/1990 | Guilbeau et al. | 5,184,359 A | 2/1993 | Tsukamura et al. |
| 4,936,956 A | 6/1990 | Wrighton | 5,185,256 A | 2/1993 | Nankai et al. |
| 4,938,860 A | 7/1990 | Wogoman | 5,190,041 A | 3/1993 | Palti |
| 4,942,127 A | 7/1990 | Wada et al. | 5,192,415 A | 3/1993 | Yoshioka et al. |
| 4,944,299 A | 7/1990 | Silvian | 5,192,416 A | 3/1993 | Wang et al. |
| 4,945,045 A | 7/1990 | Forrest et al. | 5,193,539 A | 3/1993 | Schulman et al. |
| 4,950,378 A | 8/1990 | Nagata | 5,193,540 A | 3/1993 | Schulman et al. |
| 4,953,552 A | 9/1990 | DeMarzo | 5,197,322 A | 3/1993 | Indravudh |
| 4,954,129 A | 9/1990 | Giuliani et al. | 5,198,367 A | 3/1993 | Aizawa et al. |
| 4,957,115 A | 9/1990 | Selker | 5,200,051 A | 4/1993 | Cozzette et al. |
| 4,958,632 A | 9/1990 | Duggan | 5,202,261 A | 4/1993 | Musho et al. |
| 4,968,400 A | 11/1990 | Shimomura et al. | 5,205,920 A | 4/1993 | Oyama et al. |
| 4,969,468 A | 11/1990 | Byers et al. | 5,206,145 A | 4/1993 | Cattell |
| 4,970,145 A | 11/1990 | Bennetto et al. | 5,208,154 A | 5/1993 | Weaver et al. |
| 4,974,929 A | 12/1990 | Curry | 5,209,229 A | 5/1993 | Gilli |
| 4,979,509 A | 12/1990 | Hakky | 5,215,887 A | 6/1993 | Saito |
| 4,986,271 A | 1/1991 | Wilkins | 5,216,597 A | 6/1993 | Beckers |
| 4,990,845 A | 2/1991 | Gord | 5,217,442 A | 6/1993 | Davis |
| 4,991,582 A | 2/1991 | Byers et al. | 5,217,595 A | 6/1993 | Smith et al. |
| 4,994,068 A | 2/1991 | Hufnagle | 5,227,042 A | 7/1993 | Zawodzinski et al. |
| 4,994,167 A | 2/1991 | Shults et al. | 5,229,282 A | 7/1993 | Yoshioka et al. |
| 4,995,402 A | 2/1991 | Smith et al. | 5,236,143 A | 8/1993 | Dragon |
| 5,000,180 A | 3/1991 | Kuypers et al. | 5,237,993 A | 8/1993 | Skrabal |
| 5,001,054 A | 3/1991 | Wagner | 5,246,867 A | 9/1993 | Lakowicz et al. |
| 5,002,054 A | 3/1991 | Ash et al. | 5,250,439 A | 10/1993 | Musho et al. |
| 5,007,427 A | 4/1991 | Suzuki et al. | 5,251,126 A | 10/1993 | Kahn et al. |
| 5,016,172 A | 5/1991 | Dessertine | 5,257,971 A | 11/1993 | Lord et al. |
| 5,016,201 A | 5/1991 | Bryan et al. | 5,257,980 A | 11/1993 | Van Antwerp et al. |
| 5,019,974 A | 5/1991 | Beckers | 5,261,401 A | 11/1993 | Baker et al. |
| 5,034,192 A | 7/1991 | Wrighton et al. | 5,262,035 A | 11/1993 | Gregg et al. |
| 5,035,860 A | 7/1991 | Kleingeld et al. | 5,262,305 A | 11/1993 | Heller et al. |
| 5,036,860 A | 8/1991 | Leigh et al. | 5,264,103 A | 11/1993 | Yoshioka et al. |
| 5,036,861 A | 8/1991 | Sembrowich et al. | 5,264,104 A | 11/1993 | Gregg et al. |
| 5,037,527 A | 8/1991 | Hayashi et al. | 5,264,105 A | 11/1993 | Gregg et al. |
| 5,049,487 A | 9/1991 | Phillips et al. | 5,264,106 A | 11/1993 | McAleer et al. |
| 5,050,612 A | 9/1991 | Matsumura | 5,265,888 A | 11/1993 | Yamamoto et al. |
| 5,055,171 A | 10/1991 | Peck | 5,266,179 A | 11/1993 | Nankai et al. |
| 5,058,592 A | 10/1991 | Whisler | 5,269,212 A | 12/1993 | Peters et al. |
| 5,063,081 A | 11/1991 | Cozzette et al. | 5,271,815 A | 12/1993 | Wong |
| 5,068,536 A | 11/1991 | Rosenthal | 5,272,060 A | 12/1993 | Hamamoto et al. |
| 5,070,535 A | 12/1991 | Hochmair et al. | 5,275,159 A | 1/1994 | Griebel |
| 5,073,500 A | 12/1991 | Saito et al. | 5,278,079 A | 1/1994 | Gubinski et al. |
| 5,077,476 A | 12/1991 | Rosenthal | 5,279,294 A | 1/1994 | Anderson |
| 5,078,854 A | 1/1992 | Burgess et al. | 5,282,950 A | 2/1994 | Dietze et al. |
| 5,082,550 A | 1/1992 | Rishpon et al. | 5,284,156 A | 2/1994 | Schramm et al. |
| 5,082,786 A | 1/1992 | Nakamoto | 5,285,792 A | 2/1994 | Sjoquist et al. |
| 5,084,828 A | 1/1992 | Kaufman et al. | 5,286,362 A | 2/1994 | Hoenes et al. |
| 5,089,112 A | 2/1992 | Skotheim et al. | 5,286,364 A | 2/1994 | Yacynych et al. |
| 5,094,951 A | 3/1992 | Rosenberg | 5,288,636 A | 2/1994 | Pollmann et al. |
| 5,095,904 A | 3/1992 | Seligman et al. | 5,291,887 A | 3/1994 | Stanley et al. |
| 5,096,560 A | 3/1992 | Takai et al. | 5,293,546 A | 3/1994 | Tadros et al. |
| 5,096,836 A | 3/1992 | Macho et al. | 5,293,877 A | 3/1994 | O'Hara et al. |
| 5,097,834 A | 3/1992 | Skrabal | 5,299,571 A | 4/1994 | Mastrototaro |
| 5,101,814 A | 4/1992 | Palti | 5,304,468 A | 4/1994 | Phillips et al. |
| 5,106,365 A | 4/1992 | Hernandez | 5,307,263 A | 4/1994 | Brown |
| 5,108,564 A | 4/1992 | Szuminsky et al. | 5,309,919 A | 5/1994 | Snell et al. |
| 5,109,850 A | 5/1992 | Blanco et al. | 5,310,885 A | 5/1994 | Maier et al. |
| 5,111,539 A | 5/1992 | Hiruta et al. | 5,320,725 A | 6/1994 | Gregg et al. |
| 5,111,818 A | 5/1992 | Suzuki et al. | 5,322,063 A | 6/1994 | Allen et al. |

| | | | | | | |
|---|---|---|---|---|---|---|
| 5,324,303 | A | 6/1994 | Strong et al. | 5,514,718 A | 5/1996 | Lewis et al. |
| 5,324,316 | A | 6/1994 | Schulman et al. | 5,518,006 A | 5/1996 | Mawhirt et al. |
| 5,326,449 | A | 7/1994 | Cunningham | 5,520,787 A | 5/1996 | Hanagan et al. |
| 5,337,258 | A | 8/1994 | Dennis | 5,522,865 A | 6/1996 | Schulman et al. |
| 5,337,747 | A | 8/1994 | Neftel | 5,525,511 A | 6/1996 | D'Costa |
| 5,340,722 | A | 8/1994 | Wolfbeis et al. | 5,526,120 A | 6/1996 | Jina et al. |
| 5,342,789 | A | 8/1994 | Chick et al. | 5,527,307 A | 6/1996 | Srisathapat et al. |
| 5,352,348 | A | 10/1994 | Young et al. | 5,529,676 A | 6/1996 | Maley et al. |
| 5,356,348 | A | 10/1994 | Bellio et al. | 5,531,878 A | 7/1996 | Vadgama et al. |
| 5,356,786 | A | 10/1994 | Heller et al. | 5,538,511 A | 7/1996 | Van Antwerp et al. |
| 5,358,135 | A * | 10/1994 | Robbins et al. ............... 220/834 | 5,545,152 A | 8/1996 | Funderburk et al. |
| 5,358,514 | A | 10/1994 | Schulman et al. | 5,545,191 A | 8/1996 | Mann et al. |
| 5,360,404 | A | 11/1994 | Novacek et al. | 5,549,113 A | 8/1996 | Halleck et al. |
| 5,364,797 | A | 11/1994 | Olson et al. | 5,549,115 A | 8/1996 | Morgan et al. |
| 5,366,609 | A | 11/1994 | White et al. | 5,552,027 A | 9/1996 | Birkle et al. |
| 5,368,028 | A | 11/1994 | Palti | 5,554,166 A | 9/1996 | Lange et al. |
| 5,370,622 | A | 12/1994 | Livingston et al. | 5,556,524 A | 9/1996 | Albers |
| 5,371,687 | A | 12/1994 | Holmes, II et al. | 5,560,357 A | 10/1996 | Faupel et al. |
| 5,371,734 | A | 12/1994 | Fischer | 5,562,713 A | 10/1996 | Silvian |
| 5,372,133 | A | 12/1994 | Hogen Esch | 5,565,085 A | 10/1996 | Ikeda et al. |
| 5,372,427 | A | 12/1994 | Padovani et al. | 5,567,302 A | 10/1996 | Song et al. |
| 5,376,070 | A | 12/1994 | Purvis et al. | 5,568,806 A | 10/1996 | Cheney, II et al. |
| 5,376,251 | A | 12/1994 | Kaneko et al. | 5,569,186 A | 10/1996 | Lord et al. |
| 5,377,258 | A | 12/1994 | Bro | 5,569,212 A | 10/1996 | Brown |
| 5,378,628 | A | 1/1995 | Gratzel et al. | 5,573,647 A | 11/1996 | Maley et al. |
| 5,379,238 | A | 1/1995 | Stark | 5,575,895 A | 11/1996 | Ikeda et al. |
| 5,379,764 | A | 1/1995 | Barnes et al. | 5,580,527 A | 12/1996 | Bell et al. |
| 5,380,422 | A | 1/1995 | Negishi et al. | 5,580,794 A | 12/1996 | Allen |
| 5,382,346 | A | 1/1995 | Uenoyama et al. | 5,582,184 A | 12/1996 | Erickson et al. |
| 5,387,327 | A | 2/1995 | Khan | 5,582,697 A | 12/1996 | Ikeda et al. |
| 5,390,671 | A | 2/1995 | Lord et al. | 5,582,698 A | 12/1996 | Flaherty et al. |
| 5,391,250 | A | 2/1995 | Cheney, II et al. | 5,584,813 A | 12/1996 | Livingston et al. |
| 5,393,903 | A | 2/1995 | Gratzel et al. | 5,586,553 A | 12/1996 | Halili et al. |
| 5,395,504 | A | 3/1995 | Saurer et al. | 5,589,326 A | 12/1996 | Deng et al. |
| 5,399,823 | A | 3/1995 | McCusker | 5,593,852 A | 1/1997 | Heller et al. |
| 5,400,782 | A | 3/1995 | Beaubiah | 5,594,906 A | 1/1997 | Holmes, II et al. |
| 5,408,999 | A | 4/1995 | Singh et al. | 5,596,150 A | 1/1997 | Arndy et al. |
| 5,410,471 | A | 4/1995 | Alyfuku et al. | 5,596,994 A | 1/1997 | Bro |
| 5,410,474 | A | 4/1995 | Fox | 5,601,435 A | 2/1997 | Quy |
| 5,411,647 | A | 5/1995 | Johnson et al. | 5,601,694 A | 2/1997 | Maley et al. |
| 5,413,690 | A | 5/1995 | Kost et al. | 5,605,152 A | 2/1997 | Slate et al. |
| 5,422,246 | A | 6/1995 | Koopal et al. | 5,609,575 A | 3/1997 | Larson et al. |
| 5,425,868 | A | 6/1995 | Pedersen | 5,611,900 A | 3/1997 | Worden et al. |
| 5,431,160 | A | 7/1995 | Wilkins | 5,615,135 A | 3/1997 | Waclawsky et al. |
| 5,431,691 | A | 7/1995 | Snell et al. | 5,615,671 A | 4/1997 | Schoonen et al. |
| 5,431,921 | A | 7/1995 | Thombre | 5,616,222 A | 4/1997 | Maley et al. |
| 5,433,710 | A | 7/1995 | Van Antwerp et al. | 5,617,851 A | 4/1997 | Lipkovker |
| 5,437,973 | A | 8/1995 | Vadgama et al. | 5,623,925 A | 4/1997 | Swenson et al. |
| 5,437,999 | A | 8/1995 | Diebold et al. | 5,628,309 A | 5/1997 | Brown |
| 5,438,271 | A | 8/1995 | White et al. | 5,628,310 A | 5/1997 | Rao et al. |
| 5,445,611 | A | 8/1995 | Eppstein et al. | 5,628,890 A | 5/1997 | Carter et al. |
| 5,445,920 | A | 8/1995 | Saito | 5,629,981 A | 5/1997 | Nerlikar |
| 5,456,692 | A | 10/1995 | Smith, Jr. et al. | 5,637,095 A | 6/1997 | Nason et al. |
| 5,456,940 | A | 10/1995 | Funderburk | 5,640,764 A | 6/1997 | Strojnik |
| 5,458,140 | A | 10/1995 | Eppstein et al. | 5,640,954 A | 6/1997 | Pfeiffer et al. |
| 5,460,618 | A | 10/1995 | Harreld | 5,643,212 A | 7/1997 | Coutre et al. |
| 5,462,525 | A | 10/1995 | Srisathapat et al. | 5,647,853 A | 7/1997 | Feldmann et al. |
| 5,462,645 | A | 10/1995 | Albery et al. | 5,650,062 A | 7/1997 | Ikeda et al. |
| 5,466,218 | A | 11/1995 | Srisathapat et al. | 5,651,767 A | 7/1997 | Schulman et al. |
| 5,467,778 | A | 11/1995 | Catt et al. | 5,651,869 A | 7/1997 | Yoshioka et al. |
| 5,469,846 | A | 11/1995 | Khan | 5,653,239 A | 8/1997 | Pompei et al. |
| 5,472,317 | A | 12/1995 | Field et al. | 5,660,163 A | 8/1997 | Schulman et al. |
| 5,476,460 | A | 12/1995 | Montalvo | 5,665,065 A | 9/1997 | Colman et al. |
| 5,477,855 | A | 12/1995 | Schindler et al. | 5,665,222 A | 9/1997 | Heller et al. |
| 5,482,473 | A | 1/1996 | Lord et al. | 5,667,983 A | 9/1997 | Abel et al. |
| 5,484,404 | A | 1/1996 | Schulman et al. | 5,670,031 A | 9/1997 | Hintsche et al. |
| 5,487,751 | A | 1/1996 | Radons et al. | 5,678,571 A | 10/1997 | Brown |
| 5,491,474 | A | 2/1996 | Suni et al. | 5,679,690 A | 10/1997 | Andre et al. |
| 5,494,562 | A | 2/1996 | Maley et al. | 5,680,858 A | 10/1997 | Hansen et al. |
| 5,496,453 | A | 3/1996 | Uenoyama et al. | 5,682,233 A | 10/1997 | Brinda |
| 5,497,772 | A | 3/1996 | Schulman et al. | 5,686,717 A | 11/1997 | Knowles et al. |
| 5,501,956 | A | 3/1996 | Wada et al. | 5,695,623 A | 12/1997 | Michel et al. |
| 5,505,709 | A | 4/1996 | Funderburk | 5,695,949 A | 12/1997 | Galen et al. |
| 5,505,713 | A | 4/1996 | Van Antwerp et al. | 5,701,894 A | 12/1997 | Cherry et al. |
| 5,507,288 | A | 4/1996 | Bocker et al. | 5,704,922 A | 1/1998 | Brown |
| 5,508,171 | A | 4/1996 | Walling et al. | 5,707,502 A | 1/1998 | McCaffrey et al. |
| 5,509,410 | A | 4/1996 | Hill et al. | 5,708,247 A | 1/1998 | McAleer et al. |
| 5,514,103 | A | 5/1996 | Srisathapat et al. | 5,710,630 A | 1/1998 | Essenpreis et al. |
| 5,514,253 | A | 5/1996 | Davis et al. | 5,711,001 A | 1/1998 | Bussan et al. |

| | | | | | | |
|---|---|---|---|---|---|---|
| 5,711,297 | A | 1/1998 | Iliff et al. | 5,931,791 | A | 8/1999 | Saltzstein et al. |
| 5,711,861 | A | 1/1998 | Ward et al. | 5,933,136 | A | 8/1999 | Brown |
| 5,711,862 | A | 1/1998 | Sakoda et al. | 5,935,224 | A | 8/1999 | Svancarek et al. |
| 5,711,868 | A | 1/1998 | Maley et al. | 5,939,609 | A | 8/1999 | Knapp et al. |
| 5,718,234 | A | 2/1998 | Warden et al. | 5,940,801 | A | 8/1999 | Brown |
| 5,720,733 | A | 2/1998 | Brown | 5,942,979 | A | 8/1999 | Luppino |
| 5,720,862 | A | 2/1998 | Hamamoto et al. | 5,945,345 | A | 8/1999 | Blatt et al. |
| 5,721,783 | A | 2/1998 | Anderson | 5,947,921 | A | 9/1999 | Johnson et al. |
| 5,722,397 | A | 3/1998 | Eppstein | 5,948,512 | A | 9/1999 | Kubota et al. |
| 5,727,548 | A | 3/1998 | Hill et al. | 5,950,632 | A | 9/1999 | Reber et al. |
| 5,730,124 | A | 3/1998 | Yamauchi | 5,951,300 | A | 9/1999 | Brown |
| 5,730,654 | A | 3/1998 | Brown | 5,951,492 | A | 9/1999 | Douglas et al. |
| 5,735,273 | A | 4/1998 | Kurnik et al. | 5,951,521 | A | 9/1999 | Mastrototaro et al. |
| 5,735,285 | A | 4/1998 | Albert et al. | 5,951,836 | A | 9/1999 | McAleer et al. |
| 5,741,211 | A | 4/1998 | Renirie et al. | 5,954,643 | A | 9/1999 | Van Antwerp |
| 5,741,688 | A | 4/1998 | Oxenboll et al. | 5,954,685 | A | 9/1999 | Tierny |
| 5,746,217 | A | 5/1998 | Erickson et al. | 5,954,700 | A | 9/1999 | Kovelman |
| 5,750,926 | A | 5/1998 | Schulman et al. | 5,956,501 | A | 9/1999 | Brown |
| 5,770,028 | A | 6/1998 | Maley et al. | 5,957,854 | A | 9/1999 | Besson et al. |
| 5,771,001 | A | 6/1998 | Cobb | 5,957,890 | A | 9/1999 | Mann et al. |
| 5,771,890 | A | 6/1998 | Tamada | 5,957,958 | A | 9/1999 | Schulman et al. |
| 5,772,586 | A * | 6/1998 | Heinonen et al. ............. 600/300 | 5,960,403 | A | 9/1999 | Brown |
| 5,777,060 | A | 7/1998 | Van Antwerp | 5,961,451 | A | 10/1999 | Reber et al. |
| 5,779,665 | A | 7/1998 | Mastrototaro et al. | 5,964,993 | A | 10/1999 | Blubaugh, Jr. et al. |
| 5,781,024 | A | 7/1998 | Blomberg et al. | 5,965,380 | A | 10/1999 | Heller et al. |
| 5,782,814 | A | 7/1998 | Brown et al. | 5,968,839 | A | 10/1999 | Blatt et al. |
| 5,785,681 | A | 7/1998 | Indravudh | 5,971,922 | A | 10/1999 | Arita et al. |
| 5,786,439 | A | 7/1998 | Van Antwerp et al. | 5,971,941 | A | 10/1999 | Simons et al. |
| 5,786,584 | A | 7/1998 | Button et al. | 5,974,124 | A | 10/1999 | Schlueter, Jr. et al. |
| 5,788,678 | A | 8/1998 | Van Antwerp | 5,977,476 | A | 11/1999 | Guha et al. |
| 5,791,344 | A | 8/1998 | Schulman et al. | 5,981,294 | A | 11/1999 | Blatt et al. |
| 5,792,117 | A | 8/1998 | Brown | 5,989,409 | A | 11/1999 | Kurnik et al. |
| 5,793,292 | A * | 8/1998 | Ivey, Jr. ...................... 340/576 | 5,994,476 | A | 11/1999 | Shin et al. |
| 5,800,420 | A | 9/1998 | Gross et al. | 5,995,860 | A | 11/1999 | Sun et al. |
| 5,804,048 | A | 9/1998 | Wong et al. | 5,997,476 | A | 12/1999 | Brown |
| 5,807,315 | A | 9/1998 | Van Antwerp et al. | 5,999,848 | A | 12/1999 | Gord et al. |
| 5,807,375 | A | 9/1998 | Gross et al. | 5,999,849 | A | 12/1999 | Gord et al. |
| 5,814,599 | A | 9/1998 | Mitragotri et al. | 6,001,067 | A | 12/1999 | Shults et al. |
| 5,820,551 | A | 10/1998 | Hill et al. | 6,002,954 | A | 12/1999 | Van Antwerp et al. |
| 5,820,570 | A | 10/1998 | Erickson et al. | 6,002,961 | A | 12/1999 | Mitragotri et al. |
| 5,820,622 | A | 10/1998 | Gross et al. | 6,004,441 | A | 12/1999 | Fujiwara et al. |
| 5,822,715 | A | 10/1998 | Worthington et al. | 6,011,984 | A | 1/2000 | Van Antwerp et al. |
| 5,825,488 | A | 10/1998 | Kohl et al. | 6,014,577 | A | 1/2000 | Henning et al. |
| 5,827,179 | A | 10/1998 | Lichter et al. | 6,018,678 | A | 1/2000 | Mitragotri et al. |
| 5,827,183 | A | 10/1998 | Kurnik et al. | 6,023,629 | A | 2/2000 | Tamada |
| 5,827,184 | A | 10/1998 | Netherly et al. | 6,024,699 | A | 2/2000 | Surwit et al. |
| 5,828,943 | A | 10/1998 | Brown | 6,026,320 | A | 2/2000 | Carlson et al. |
| 5,830,341 | A | 11/1998 | Gilmartin | 6,027,459 | A | 2/2000 | Shain et al. |
| 5,832,448 | A | 11/1998 | Brown | 6,027,692 | A | 2/2000 | Galen et al. |
| 5,834,224 | A | 11/1998 | Ruger et al. | 6,032,059 | A | 2/2000 | Henning et al. |
| 5,837,454 | A | 11/1998 | Cozzette et al. | 6,032,119 | A | 2/2000 | Brown et al. |
| 5,837,546 | A | 11/1998 | Allen et al. | 6,033,866 | A | 3/2000 | Guo et al. |
| 5,840,020 | A | 11/1998 | Heinonen et al. | 6,035,237 | A | 3/2000 | Schulman et al. |
| 5,842,983 | A | 12/1998 | Abel et al. | 6,040,194 | A | 3/2000 | Chick et al. |
| 5,843,140 | A | 12/1998 | Strojnik | 6,041,253 | A | 3/2000 | Kost et al. |
| 5,846,702 | A | 12/1998 | Deng et al. | 6,043,437 | A | 3/2000 | Schulman et al. |
| 5,846,744 | A | 12/1998 | Athey et al. | 6,049,727 | A | 4/2000 | Crothall |
| 5,851,197 | A | 12/1998 | Marano et al. | D424,696 | S | 5/2000 | Ray et al. |
| 5,854,078 | A | 12/1998 | Asher et al. | 6,056,718 | A | 5/2000 | Funderburk et al. |
| 5,854,189 | A | 12/1998 | Kruse et al. | 6,063,459 | A | 5/2000 | Velte |
| 5,856,758 | A | 1/1999 | Joffe et al. | 6,066,243 | A | 5/2000 | Anderson et al. |
| 5,857,967 | A | 1/1999 | Frid et al. | 6,067,474 | A | 5/2000 | Schulman et al. |
| 5,857,983 | A | 1/1999 | Douglas et al. | 6,068,615 | A | 5/2000 | Brown et al. |
| 5,860,917 | A | 1/1999 | Comanor et al. | D426,638 | S | 6/2000 | Ray et al. |
| 5,872,713 | A | 2/1999 | Douglas et al. | D427,312 | S | 6/2000 | Douglas |
| 5,876,484 | A | 3/1999 | Raskin et al. | 6,071,249 | A | 6/2000 | Cunningham et al. |
| 5,879,163 | A | 3/1999 | Brown et al. | 6,071,251 | A | 6/2000 | Cunningham et al. |
| 5,879,311 | A | 3/1999 | Duchon et al. | 6,071,294 | A | 6/2000 | Simons et al. |
| 5,880,829 | A | 3/1999 | Kauhaniemi et al. | 6,071,391 | A | 6/2000 | Gotoh et al. |
| 5,882,494 | A | 3/1999 | Van Antwerp | 6,073,031 | A | 6/2000 | Helstab et al. |
| 5,885,211 | A | 3/1999 | Eppstein et al. | 6,081,736 | A | 6/2000 | Colvin et al. |
| 5,887,133 | A | 3/1999 | Brown et al. | 6,083,710 | A | 7/2000 | Heller et al. |
| 5,897,493 | A | 4/1999 | Brown | 6,088,608 | A | 7/2000 | Schulman et al. |
| 5,898,025 | A | 4/1999 | Burg et al. | 6,091,975 | A | 7/2000 | Daddona et al. |
| 5,899,855 | A | 5/1999 | Brown | 6,091,976 | A | 7/2000 | Pfeiffer et al. |
| 5,913,310 | A | 6/1999 | Brown | 6,093,156 | A | 7/2000 | Cunningham et al. |
| 5,917,346 | A | 6/1999 | Gord | 6,093,167 | A | 7/2000 | Houben et al. |
| 5,918,603 | A | 7/1999 | Brown | 6,093,172 | A | 7/2000 | Funderburk et al. |
| 5,925,021 | A | 7/1999 | Castellano et al. | 6,097,480 | A * | 8/2000 | Kaplan ........................ 356/139 |

| | | | |
|---|---|---|---|
| 6,097,831 A | 8/2000 | Wieck et al. | |
| 6,099,484 A | 8/2000 | Douglas et al. | |
| 6,101,478 A | 8/2000 | Brown | |
| 6,103,033 A | 8/2000 | Say et al. | |
| 6,106,780 A | 8/2000 | Douglas et al. | |
| 6,110,148 A | 8/2000 | Brown et al. | |
| 6,110,152 A | 8/2000 | Kovelman | |
| 6,113,578 A | 9/2000 | Brown | |
| 6,117,290 A | 9/2000 | Say et al. | |
| 6,119,028 A | 9/2000 | Schulman et al. | |
| 6,120,676 A | 9/2000 | Heller et al. | |
| 6,121,009 A | 9/2000 | Heller et al. | |
| 6,121,611 A | 9/2000 | Lindsay et al. | |
| 6,122,351 A | 9/2000 | Schlueter, Jr. et al. | |
| 6,125,978 A | 10/2000 | Ando et al. | |
| 6,134,461 A | 10/2000 | Say et al. | |
| 6,134,504 A | 10/2000 | Douglas et al. | |
| 6,139,718 A | 10/2000 | Kurnik et al. | |
| 6,141,573 A | 10/2000 | Kurnik et al. | |
| 6,142,939 A | 11/2000 | Eppstein et al. | |
| 6,143,164 A | 11/2000 | Heller et al. | |
| 6,144,837 A | 11/2000 | Quy | |
| 6,144,869 A | 11/2000 | Berner et al. | |
| 6,144,922 A | 11/2000 | Douglas et al. | |
| 6,148,094 A | 11/2000 | Kinsella | |
| 6,150,128 A | 11/2000 | Uretsky | |
| 6,151,586 A | 11/2000 | Brown | |
| 6,153,062 A | 11/2000 | Saito et al. | |
| 6,153,069 A | 11/2000 | Pottgen et al. | |
| 6,159,147 A | 12/2000 | Lichter et al. | |
| 6,161,095 A | 12/2000 | Brown | |
| 6,162,611 A | 12/2000 | Heller et al. | |
| 6,162,639 A | 12/2000 | Douglas | |
| 6,164,284 A | 12/2000 | Schulman et al. | |
| 6,167,362 A | 12/2000 | Brown et al. | |
| 6,168,563 B1 | 1/2001 | Brown | |
| 6,170,318 B1 | 1/2001 | Lewis et al. | |
| 6,175,752 B1 | 1/2001 | Say et al. | |
| 6,180,416 B1 | 1/2001 | Kurnik et al. | |
| 6,186,145 B1 | 2/2001 | Brown | |
| 6,192,891 B1 | 2/2001 | Gravel et al. | |
| 6,193,873 B1 | 2/2001 | Ohara et al. | |
| D439,242 S | 3/2001 | Brown et al. | |
| 6,196,970 B1 | 3/2001 | Brown | |
| 6,198,957 B1 | 3/2001 | Green | |
| 6,200,265 B1 | 3/2001 | Walsh et al. | |
| 6,201,979 B1 | 3/2001 | Kurnik et al. | |
| 6,201,980 B1 | 3/2001 | Darrow et al. | |
| 6,206,841 B1 | 3/2001 | Cunningham | |
| 6,207,400 B1 | 3/2001 | Kwon | |
| 6,208,894 B1 | 3/2001 | Schulman et al. | |
| 6,210,272 B1 | 4/2001 | Brown | |
| 6,210,976 B1 | 4/2001 | Sabbadini | |
| 6,212,416 B1 | 4/2001 | Ward et al. | |
| 6,219,565 B1 | 4/2001 | Cupp et al. | |
| 6,219,574 B1 | 4/2001 | Cormier et al. | |
| 6,224,745 B1 | 5/2001 | Baltruschat | |
| 6,232,130 B1 | 5/2001 | Wolf | |
| 6,232,370 B1 | 5/2001 | Kubota et al. | |
| 6,233,471 B1 | 5/2001 | Berner et al. | |
| 6,233,539 B1 | 5/2001 | Brown | |
| 6,239,925 B1 | 5/2001 | Ardrey et al. | |
| 6,241,862 B1 | 6/2001 | McAleer et al. | |
| 6,246,330 B1 | 6/2001 | Nielsen | |
| 6,246,992 B1 | 6/2001 | Brown | |
| 6,248,065 B1 | 6/2001 | Brown | |
| 6,248,067 B1 | 6/2001 | Causey, III et al. | |
| 6,248,093 B1 | 6/2001 | Moberg | |
| 6,251,260 B1 | 6/2001 | Heller et al. | |
| 6,252,032 B1 | 6/2001 | Van Antwerp et al. | |
| 6,253,804 B1 | 7/2001 | Safabash | |
| 6,254,586 B1 | 7/2001 | Mann et al. | |
| 6,256,643 B1 | 7/2001 | Cork et al. | |
| 6,259,587 B1 | 7/2001 | Sheldon et al. | |
| 6,259,937 B1 | 7/2001 | Schulman et al. | |
| 6,260,022 B1 | 7/2001 | Brown | |
| 6,266,645 B1 | 7/2001 | Simpson | |
| 6,267,724 B1 | 7/2001 | Taylor | |
| 6,268,161 B1 | 7/2001 | Han et al. | |
| 6,270,455 B1 | 8/2001 | Brown | |
| 6,272,364 B1 | 8/2001 | Kurnik | |
| 6,275,717 B1 | 8/2001 | Gross et al. | |
| 6,280,416 B1 | 8/2001 | Van Antwerp et al. | |
| 6,280,587 B1 | 8/2001 | Matsumoto | |
| 6,281,006 B1 | 8/2001 | Heller et al. | |
| 6,283,943 B1 | 9/2001 | Dy et al. | |
| 6,284,126 B1 | 9/2001 | Kurnik et al. | |
| 6,284,478 B1 | 9/2001 | Heller et al. | |
| 6,293,925 B1 | 9/2001 | Safabash et al. | |
| 6,294,281 B1 | 9/2001 | Heller | |
| 6,295,463 B1 | 9/2001 | Stenzler | |
| 6,295,506 B1 * | 9/2001 | Heinonen et al. ............. 702/104 |
| 6,298,254 B2 | 10/2001 | Tamada | |
| 6,299,578 B1 | 10/2001 | Kurnik et al. | |
| 6,299,757 B1 | 10/2001 | Feldman et al. | |
| 6,301,499 B1 | 10/2001 | Carlson et al. | |
| 6,304,766 B1 | 10/2001 | Colvin, Jr. et al. | |
| 6,306,104 B1 | 10/2001 | Cunningham et al. | |
| 6,307,867 B1 | 10/2001 | Roobol et al. | |
| 6,309,351 B1 | 10/2001 | Kurnik et al. | |
| 6,309,884 B1 | 10/2001 | Cooper et al. | |
| 6,315,721 B2 | 11/2001 | Schulman et al. | |
| 6,319,540 B1 | 11/2001 | Van Antwerp et al. | |
| 6,326,160 B1 | 12/2001 | Dunn et al. | |
| 6,329,161 B1 | 12/2001 | Heller et al. | |
| 6,329,929 B1 | 12/2001 | Weijand et al. | |
| 6,330,426 B2 | 12/2001 | Brown et al. | |
| 6,330,464 B1 | 12/2001 | Colvin, Jr. et al. | |
| 6,331,518 B2 | 12/2001 | Hemm et al. | |
| 6,334,778 B1 | 1/2002 | Brown | |
| 6,338,790 B1 | 1/2002 | Feldman et al. | |
| 6,340,421 B1 | 1/2002 | Vachon et al. | |
| 6,341,232 B1 | 1/2002 | Conn et al. | |
| 6,356,776 B1 | 3/2002 | Berner et al. | |
| 6,360,888 B1 | 3/2002 | McIvor et al. | |
| 6,366,793 B1 | 4/2002 | Bell et al. | |
| 6,366,794 B1 | 4/2002 | Moussy et al. | |
| 6,368,141 B1 | 4/2002 | Van Antwerp et al. | |
| 6,368,274 B1 | 4/2002 | Van Antwerp et al. | |
| 6,370,410 B2 | 4/2002 | Kurnik et al. | |
| 6,377,828 B1 | 4/2002 | Chaiken et al. | |
| 6,379,301 B1 | 4/2002 | Worthington et al. | |
| 6,383,767 B1 | 5/2002 | Polak | |
| 6,387,048 B1 | 5/2002 | Schulman et al. | |
| 6,391,643 B1 | 5/2002 | Chen et al. | |
| 6,393,318 B1 | 5/2002 | Conn et al. | |
| 6,398,562 B1 | 6/2002 | Butler et al. | |
| 6,405,066 B1 | 6/2002 | Essenpreis et al. | |
| 6,413,393 B1 | 7/2002 | Van Antwerp et al. | |
| 6,416,471 B1 | 7/2002 | Kumar et al. | |
| 6,418,332 B1 | 7/2002 | Mastrototaro et al. | |
| 6,424,847 B1 | 7/2002 | Mastrototaro et al. | |
| 6,427,088 B1 | 7/2002 | Bowman, IV et al. | |
| 6,434,409 B1 | 8/2002 | Pfeiffer et al. | |
| 6,438,414 B1 | 8/2002 | Conn et al. | |
| 6,440,068 B1 * | 8/2002 | Brown et al. ................. 600/300 |
| 6,442,637 B1 | 8/2002 | Hawkins et al. | |
| 6,443,942 B2 | 9/2002 | Van Antwerp et al. | |
| 6,449,255 B1 | 9/2002 | Waclawsky et al. | |
| 6,454,710 B1 | 9/2002 | Ballerstadt et al. | |
| 6,462,162 B2 | 10/2002 | Van Antwerp et al. | |
| 6,464,848 B1 | 10/2002 | Matsumoto | |
| 6,466,810 B1 | 10/2002 | Ward et al. | |
| 6,468,222 B1 | 10/2002 | Mault et al. | |
| 6,472,122 B1 | 10/2002 | Schulman et al. | |
| 6,475,750 B1 | 11/2002 | Han et al. | |
| 6,477,395 B2 | 11/2002 | Schulman et al. | |
| 6,478,736 B1 * | 11/2002 | Mault ........................ 600/300 |
| 6,480,730 B2 | 11/2002 | Darrow et al. | |
| 6,482,156 B2 | 11/2002 | Iliff | |
| 6,482,158 B2 | 11/2002 | Mault | |
| 6,482,604 B2 | 11/2002 | Kwon | |
| 6,484,045 B1 | 11/2002 | Holker et al. | |
| 6,484,046 B1 | 11/2002 | Say et al. | |
| 6,485,138 B1 | 11/2002 | Kubota et al. | |
| 6,494,830 B1 | 12/2002 | Wessel | |
| 6,496,728 B2 | 12/2002 | Li et al. | |
| 6,505,059 B1 | 1/2003 | Kollias et al. | |

| | | | |
|---|---|---|---|
| 6,505,121 B1 * | 1/2003 | Russell .................. 701/213 |
| 6,512,939 B1 | 1/2003 | Colvin et al. |
| 6,513,532 B2 | 2/2003 | Mault et al. |
| 6,514,718 B2 | 2/2003 | Heller et al. |
| 6,515,593 B1 | 2/2003 | Stark et al. |
| 6,520,326 B2 | 2/2003 | McIvor et al. |
| 6,529,755 B2 | 3/2003 | Kurnik et al. |
| 6,529,772 B2 | 3/2003 | Carlson et al. |
| 6,530,915 B1 | 3/2003 | Eppstein et al. |
| 6,534,322 B1 | 3/2003 | Sabbadini |
| 6,534,323 B1 | 3/2003 | Sabbadini |
| 6,535,753 B1 | 3/2003 | Raskas |
| 6,537,243 B1 | 3/2003 | Henning et al. |
| 6,540,675 B2 | 4/2003 | Aceti et al. |
| 6,541,266 B2 * | 4/2003 | Modzelewski et al. ......... 436/95 |
| 6,544,212 B2 | 4/2003 | Galley et al. |
| 6,546,269 B1 | 4/2003 | Kurnik |
| 6,549,796 B2 | 4/2003 | Sohrab |
| 6,551,276 B1 | 4/2003 | Mann et al. |
| 6,551,494 B1 | 4/2003 | Heller et al. |
| 6,553,244 B2 | 4/2003 | Lesho et al. |
| 6,554,798 B1 | 4/2003 | Mann et al. |
| 6,558,320 B1 | 5/2003 | Causey, III et al. |
| 6,558,321 B1 | 5/2003 | Burd et al. |
| 6,558,351 B1 | 5/2003 | Steil et al. |
| 6,560,471 B1 | 5/2003 | Heller et al. |
| 6,561,978 B1 * | 5/2003 | Conn et al. ................ 600/309 |
| 6,562,001 B2 | 5/2003 | Lebel et al. |
| 6,564,105 B2 | 5/2003 | Starkweather et al. |
| 6,564,807 B1 | 5/2003 | Schulman et al. |
| 6,565,509 B1 | 5/2003 | Say et al. |
| 6,571,128 B2 | 5/2003 | Lebel et al. |
| 6,571,200 B1 | 5/2003 | Mault |
| 6,576,101 B1 | 6/2003 | Heller et al. |
| 6,576,117 B1 | 6/2003 | Iketaki et al. |
| 6,577,899 B2 | 6/2003 | Lebel et al. |
| 6,579,498 B1 | 6/2003 | Eglise |
| 6,579,690 B1 | 6/2003 | Bonnecaze et al. |
| 6,584,335 B1 | 6/2003 | Haar et al. |
| 6,585,644 B2 | 7/2003 | Lebel et al. |
| 6,587,705 B1 | 7/2003 | Kim et al. |
| 6,591,125 B1 | 7/2003 | Buse et al. |
| 6,591,126 B2 | 7/2003 | Roeper et al. |
| 6,594,514 B2 | 7/2003 | Berner et al. |
| 6,595,919 B2 | 7/2003 | Berner et al. |
| 6,595,929 B2 * | 7/2003 | Stivoric et al. ............ 600/549 |
| 6,599,243 B2 * | 7/2003 | Woltermann et al. ......... 600/300 |
| 6,602,678 B2 | 8/2003 | Kwon et al. |
| 6,602,909 B1 | 8/2003 | Jarowski |
| 6,605,200 B1 | 8/2003 | Mao et al. |
| 6,605,201 B1 | 8/2003 | Mao et al. |
| 6,607,509 B2 | 8/2003 | Bobroff et al. |
| 6,610,012 B2 | 8/2003 | Mault |
| 6,612,306 B1 | 9/2003 | Mault |
| 6,615,078 B1 | 9/2003 | Burson et al. |
| 6,618,603 B2 | 9/2003 | Varalli et al. |
| 6,620,106 B2 | 9/2003 | Mault |
| 6,627,058 B1 | 9/2003 | Chan |
| 6,629,934 B2 | 10/2003 | Mault et al. |
| 6,633,772 B2 | 10/2003 | Ford et al. |
| 6,635,014 B2 | 10/2003 | Starkweather et al. |
| 6,641,533 B2 | 11/2003 | Causey, III et al. |
| 6,642,015 B2 | 11/2003 | Vachon et al. |
| 6,645,142 B2 | 11/2003 | Braig et al. |
| 6,645,368 B1 | 11/2003 | Beaty et al. |
| 6,648,821 B2 | 11/2003 | Lebel et al. |
| 6,653,091 B1 | 11/2003 | Dunn et al. |
| 6,654,625 B1 | 11/2003 | Say et al. |
| 6,659,948 B2 | 12/2003 | Lebel et al. |
| 6,668,196 B1 | 12/2003 | Villegas et al. |
| 6,671,554 B2 | 12/2003 | Gibson et al. |
| 6,673,625 B2 | 1/2004 | Satcher, Jr. et al. |
| 6,682,938 B1 | 1/2004 | Satcher, Jr. et al. |
| 6,683,040 B2 | 1/2004 | Bragulla et al. |
| 6,687,522 B2 | 2/2004 | Tamada |
| 6,687,546 B2 | 2/2004 | Lebel et al. |
| 6,689,056 B1 | 2/2004 | Kilcoyne et al. |
| 6,690,276 B1 | 2/2004 | Marino |
| 6,693,069 B2 | 2/2004 | Korber et al. |
| 6,694,158 B2 | 2/2004 | Polak |
| 6,694,191 B2 | 2/2004 | Starkweather et al. |
| 6,695,860 B1 | 2/2004 | Ward et al. |
| 6,698,269 B2 | 3/2004 | Baber et al. |
| 6,702,857 B2 | 3/2004 | Brauker et al. |
| 6,704,587 B1 | 3/2004 | Kumar et al. |
| 6,711,423 B2 | 3/2004 | Colvin, Jr. |
| 6,723,046 B2 | 4/2004 | Lichtenstein et al. |
| 6,728,560 B2 | 4/2004 | Kollias et al. |
| 6,731,976 B2 | 5/2004 | Penn et al. |
| 6,733,446 B2 | 5/2004 | Lebel et al. |
| 6,734,162 B2 | 5/2004 | Van Antwerp et al. |
| 6,736,777 B2 | 5/2004 | Kim et al. |
| 6,736,797 B1 | 5/2004 | Larsen et al. |
| 6,737,401 B2 | 5/2004 | Kim et al. |
| 6,738,654 B2 | 5/2004 | Sohrab |
| 6,740,075 B2 | 5/2004 | Lebel et al. |
| 6,741,163 B1 | 5/2004 | Roberts |
| 6,741,876 B1 | 5/2004 | Scecina et al. |
| 6,741,877 B1 | 5/2004 | Shults et al. |
| 6,746,582 B2 | 6/2004 | Heller et al. |
| 6,749,587 B2 | 6/2004 | Flaherty |
| 6,750,311 B1 | 6/2004 | Van Antwerp et al. |
| 6,758,810 B2 | 7/2004 | Lebel et al. |
| 6,766,183 B2 | 7/2004 | Walsh et al. |
| 6,766,201 B2 | 7/2004 | Von Arx et al. |
| 6,768,425 B2 | 7/2004 | Flaherty et al. |
| 6,770,030 B1 | 8/2004 | Schaupp et al. |
| 6,770,729 B2 | 8/2004 | Van Antwerp et al. |
| 6,771,995 B2 | 8/2004 | Kurnik et al. |
| 6,773,563 B2 | 8/2004 | Matsumoto |
| 6,780,156 B2 | 8/2004 | Haueter et al. |
| 6,780,297 B2 | 8/2004 | Matsumoto et al. |
| 6,780,871 B2 | 8/2004 | Glick et al. |
| 6,784,274 B2 | 8/2004 | Van Antwerp et al. |
| 6,790,178 B1 | 9/2004 | Mault et al. |
| 6,794,195 B2 | 9/2004 | Colvin, Jr. |
| 6,800,451 B2 | 10/2004 | Daniloff et al. |
| 6,804,544 B2 | 10/2004 | Van Antwerp et al. |
| 6,809,507 B2 | 10/2004 | Morgan et al. |
| 6,809,653 B1 | 10/2004 | Mann et al. |
| 6,810,290 B2 | 10/2004 | Lebel et al. |
| 6,810,309 B2 * | 10/2004 | Sadler et al. ................... 701/1 |
| 6,811,533 B2 | 11/2004 | Lebel et al. |
| 6,811,534 B2 | 11/2004 | Bowman, IV et al. |
| 6,811,659 B2 | 11/2004 | Vachon |
| 6,812,031 B1 | 11/2004 | Carlsson |
| 6,813,519 B2 | 11/2004 | Lebel et al. |
| 6,816,742 B2 | 11/2004 | Kim et al. |
| 6,835,553 B2 | 12/2004 | Han et al. |
| RE38,681 E | 1/2005 | Kurnik et al. |
| 6,840,912 B2 | 1/2005 | Kloepfer et al. |
| 6,844,023 B2 | 1/2005 | Schulman et al. |
| 6,849,237 B2 | 2/2005 | Housefield et al. |
| 6,850,790 B2 | 2/2005 | Berner et al. |
| 6,852,104 B2 | 2/2005 | Blomquist |
| 6,852,500 B1 | 2/2005 | Hoss et al. |
| 6,852,694 B2 | 2/2005 | Van Antwerp et al. |
| 6,853,854 B1 | 2/2005 | Proniewicz et al. |
| 6,856,928 B2 | 2/2005 | Harmon |
| 6,858,403 B2 | 2/2005 | Han et al. |
| 6,862,465 B2 | 3/2005 | Shults et al. |
| 6,862,466 B2 | 3/2005 | Ackerman |
| 6,872,200 B2 | 3/2005 | Mann et al. |
| 6,873,268 B2 | 3/2005 | Lebel et al. |
| 6,881,551 B2 | 4/2005 | Heller et al. |
| 6,882,940 B2 | 4/2005 | Potts et al. |
| 6,885,883 B2 | 4/2005 | Parris et al. |
| 6,892,085 B2 | 5/2005 | McIvor et al. |
| 6,895,263 B2 | 5/2005 | Shin et al. |
| 6,895,265 B2 | 5/2005 | Silver |
| 6,899,683 B2 | 5/2005 | Mault et al. |
| 6,899,684 B2 | 5/2005 | Mault et al. |
| 6,902,207 B2 | 6/2005 | Lickliter |
| 6,902,905 B2 | 6/2005 | Burson et al. |
| 6,904,301 B2 | 6/2005 | Raskas |
| 6,907,127 B1 | 6/2005 | Kravitz et al. |
| 6,915,147 B2 | 7/2005 | Lebel et al. |
| 6,918,874 B1 | 7/2005 | Hatch et al. |

| | | |
|---|---|---|
| 6,922,578 B2 | 7/2005 | Eppstein et al. |
| RE38,775 E | 8/2005 | Kurnik et al. |
| 6,923,764 B2 | 8/2005 | Aceti et al. |
| 6,923,936 B2 | 8/2005 | Swanson et al. |
| 6,927,246 B2 | 8/2005 | Noronha et al. |
| 6,931,327 B2 | 8/2005 | Goode, Jr. et al. |
| 6,932,894 B2 | 8/2005 | Mao et al. |
| 6,936,006 B2 | 8/2005 | Sabra |
| 6,936,029 B2 | 8/2005 | Mann et al. |
| 6,940,590 B2 | 9/2005 | Colvin, Jr. et al. |
| 6,941,163 B2 | 9/2005 | Ford et al. |
| 6,950,708 B2 | 9/2005 | Bowman, IV et al. |
| 6,952,603 B2 | 10/2005 | Gerber et al. |
| 6,954,673 B2 | 10/2005 | Von Arx et al. |
| 6,955,650 B2 | 10/2005 | Mault et al. |
| 6,957,102 B2 | 10/2005 | Silver et al. |
| 6,957,107 B2 | 10/2005 | Rogers et al. |
| 6,958,705 B2 | 10/2005 | Lebel et al. |
| 6,968,294 B2 | 11/2005 | Gutta et al. |
| 6,968,375 B1 | 11/2005 | Brown |
| 6,971,274 B2 | 12/2005 | Olin |
| 6,974,437 B2 | 12/2005 | Lebel et al. |
| 6,978,182 B2 | 12/2005 | Mazar et al. |
| 6,979,326 B2 | 12/2005 | Mann et al. |
| 6,985,870 B2 | 1/2006 | Martucci et al. |
| 6,990,366 B2 | 1/2006 | Say et al. |
| 6,991,096 B2 | 1/2006 | Gottlieb et al. |
| 6,997,907 B2 | 2/2006 | Safabash et al. |
| 6,997,920 B2 | 2/2006 | Mann et al. |
| 6,998,247 B2 | 2/2006 | Monfre et al. |
| 6,999,810 B2 | 2/2006 | Berner et al. |
| 7,003,336 B2 | 2/2006 | Holker et al. |
| 7,003,340 B2 | 2/2006 | Say et al. |
| 7,003,341 B2 | 2/2006 | Say et al. |
| 7,004,901 B2 | 2/2006 | Fish |
| 7,005,857 B2 | 2/2006 | Stiene et al. |
| 7,011,630 B2 | 3/2006 | Desai et al. |
| 7,018,366 B2 | 3/2006 | Easter |
| 7,018,568 B2 | 3/2006 | Tierney |
| 7,022,072 B2 | 4/2006 | Fox et al. |
| 7,024,236 B2 | 4/2006 | Ford et al. |
| 7,024,245 B2 | 4/2006 | Lebel et al. |
| 7,025,743 B2 | 4/2006 | Mann et al. |
| 7,027,621 B1 * | 4/2006 | Prokoski ............... 180/272 |
| 7,029,444 B2 | 4/2006 | Shin et al. |
| 7,039,810 B1 | 5/2006 | Nichols |
| 7,041,068 B2 | 5/2006 | Freeman et al. |
| 7,041,468 B2 | 5/2006 | Drucker et al. |
| 7,049,277 B2 | 5/2006 | Bragulla et al. |
| 7,052,251 B2 | 5/2006 | Nason et al. |
| 7,052,472 B1 | 5/2006 | Miller et al. |
| 7,052,483 B2 | 5/2006 | Wojcik |
| 7,056,302 B2 | 6/2006 | Douglas |
| 7,060,030 B2 | 6/2006 | Von Arx et al. |
| 7,074,307 B2 | 7/2006 | Simpson et al. |
| 7,081,195 B2 | 7/2006 | Simpson et al. |
| 7,098,803 B2 | 8/2006 | Mann et al. |
| 7,108,778 B2 | 9/2006 | Simpson et al. |
| 7,110,803 B2 | 9/2006 | Shults et al. |
| 7,113,821 B1 | 9/2006 | Sun et al. |
| 7,125,382 B2 | 10/2006 | Zhou et al. |
| 7,133,710 B2 | 11/2006 | Acosta et al. |
| 7,134,999 B2 | 11/2006 | Brauker et al. |
| 7,136,689 B2 | 11/2006 | Shults et al. |
| 7,150,975 B2 | 12/2006 | Tamada et al. |
| 7,155,112 B2 | 12/2006 | Uno et al. |
| 7,163,511 B2 | 1/2007 | Conn et al. |
| 7,171,274 B2 | 1/2007 | Starkweather et al. |
| 7,183,068 B2 | 2/2007 | Burson et al. |
| 7,183,102 B2 | 2/2007 | Monfre et al. |
| 7,189,341 B2 | 3/2007 | Li et al. |
| 7,190,988 B2 | 3/2007 | Say et al. |
| 7,192,450 B2 | 3/2007 | Brauker et al. |
| 7,198,606 B2 | 4/2007 | Boecker et al. |
| 7,226,978 B2 | 6/2007 | Tapsak et al. |
| 7,228,163 B2 | 6/2007 | Ackerman |
| 7,233,817 B2 | 6/2007 | Yen |
| 7,241,266 B2 | 7/2007 | Zhou et al. |
| 7,261,691 B1 | 8/2007 | Asomani |
| 7,267,665 B2 | 9/2007 | Steil et al. |
| 7,276,029 B2 | 10/2007 | Goode, Jr. et al. |
| 7,278,983 B2 | 10/2007 | Ireland et al. |
| 7,291,107 B2 | 11/2007 | Hellwig et al. |
| 7,295,867 B2 | 11/2007 | Berner et al. |
| 7,297,112 B2 | 11/2007 | Zhou et al. |
| 7,299,082 B2 | 11/2007 | Feldman et al. |
| 7,310,544 B2 | 12/2007 | Brister et al. |
| 7,324,012 B2 | 1/2008 | Mann et al. |
| 7,335,294 B2 | 2/2008 | Heller et al. |
| 7,354,420 B2 | 4/2008 | Steil et al. |
| 7,364,592 B2 | 4/2008 | Carr-Brendel et al. |
| 7,366,556 B2 | 4/2008 | Brister et al. |
| 7,379,765 B2 | 5/2008 | Petisce et al. |
| 7,398,183 B2 | 7/2008 | Holland et al. |
| 7,402,153 B2 | 7/2008 | Steil et al. |
| 7,424,318 B2 | 9/2008 | Brister et al. |
| 7,460,898 B2 | 12/2008 | Brister et al. |
| 7,467,003 B2 | 12/2008 | Brister et al. |
| 7,471,972 B2 | 12/2008 | Rhodes et al. |
| 7,494,465 B2 | 2/2009 | Brister et al. |
| 7,497,827 B2 | 3/2009 | Brister et al. |
| 7,519,408 B2 | 4/2009 | Rasdal et al. |
| 7,547,281 B2 | 6/2009 | Hayes et al. |
| 7,569,030 B2 | 8/2009 | Lebel et al. |
| 7,583,990 B2 | 9/2009 | Goode, Jr. et al. |
| 7,591,801 B2 | 9/2009 | Brauker et al. |
| 7,599,726 B2 | 10/2009 | Goode, Jr. et al. |
| 7,613,491 B2 | 11/2009 | Boock et al. |
| 7,615,007 B2 | 11/2009 | Shults et al. |
| 7,618,369 B2 | 11/2009 | Hayter et al. |
| 7,632,228 B2 | 12/2009 | Brauker et al. |
| 7,637,868 B2 | 12/2009 | Saint et al. |
| 7,640,048 B2 | 12/2009 | Dobbles et al. |
| 7,651,596 B2 | 1/2010 | Petisce et al. |
| 7,654,956 B2 | 2/2010 | Brister et al. |
| 7,657,297 B2 | 2/2010 | Simpson et al. |
| 7,711,402 B2 | 5/2010 | Shults et al. |
| 7,713,574 B2 | 5/2010 | Brister et al. |
| 7,715,893 B2 | 5/2010 | Kamath et al. |
| 2001/0011224 A1 | 8/2001 | Brown |
| 2001/0016310 A1 | 8/2001 | Brown et al. |
| 2001/0016682 A1 | 8/2001 | Berner et al. |
| 2001/0016683 A1 | 8/2001 | Darrow et al. |
| 2001/0020124 A1 | 9/2001 | Tamada |
| 2001/0029340 A1 | 10/2001 | Mault et al. |
| 2001/0032278 A1 | 10/2001 | Brown et al. |
| 2001/0037060 A1 | 11/2001 | Thompson et al. |
| 2001/0037069 A1 | 11/2001 | Carlson et al. |
| 2001/0039504 A1 | 11/2001 | Linberg et al. |
| 2001/0041830 A1 | 11/2001 | Varalli et al. |
| 2001/0041831 A1 | 11/2001 | Starkweather et al. |
| 2001/0044581 A1 | 11/2001 | Mault |
| 2001/0044588 A1 | 11/2001 | Mault |
| 2001/0047125 A1 | 11/2001 | Quy |
| 2001/0049096 A1 | 12/2001 | Brown |
| 2001/0049470 A1 | 12/2001 | Mault et al. |
| 2002/0002326 A1 | 1/2002 | Causey, III et al. |
| 2002/0002328 A1 | 1/2002 | Tamada |
| 2002/0004640 A1 | 1/2002 | Conn et al. |
| 2002/0010414 A1 | 1/2002 | Coston et al. |
| 2002/0016530 A1 | 2/2002 | Brown |
| 2002/0016719 A1 | 2/2002 | Nemeth et al. |
| 2002/0019022 A1 | 2/2002 | Dunn et al. |
| 2002/0019586 A1 | 2/2002 | Teller et al. |
| 2002/0019748 A1 | 2/2002 | Brown |
| 2002/0026937 A1 | 3/2002 | Mault |
| 2002/0027164 A1 | 3/2002 | Mault et al. |
| 2002/0028995 A1 | 3/2002 | Mault |
| 2002/0040208 A1 | 4/2002 | Flaherty et al. |
| 2002/0042090 A1 | 4/2002 | Heller et al. |
| 2002/0047867 A1 | 4/2002 | Mault et al. |
| 2002/0053637 A1 | 5/2002 | Conn et al. |
| 2002/0062069 A1 | 5/2002 | Mault |
| 2002/0063060 A1 | 5/2002 | Gascoyne et al. |
| 2002/0068858 A1 | 6/2002 | Braig et al. |
| 2002/0072858 A1 | 6/2002 | Cheng |
| 2002/0077765 A1 | 6/2002 | Mault |
| 2002/0077766 A1 | 6/2002 | Mault |

| | | |
|---|---|---|
| 2002/0081559 A1 | 6/2002 | Brown et al. |
| 2002/0083461 A1 | 6/2002 | Hutcheson et al. |
| 2002/0087056 A1 | 7/2002 | Aceti et al. |
| 2002/0091312 A1 | 7/2002 | Berner et al. |
| 2002/0103425 A1 | 8/2002 | Mault |
| 2002/0103499 A1 | 8/2002 | Perez et al. |
| 2002/0106709 A1 | 8/2002 | Potts et al. |
| 2002/0107433 A1 | 8/2002 | Mault |
| 2002/0107476 A1 | 8/2002 | Mann et al. |
| 2002/0109600 A1 | 8/2002 | Mault et al. |
| 2002/0119711 A1 | 8/2002 | Van Antwerp et al. |
| 2002/0124017 A1 | 9/2002 | Mault |
| 2002/0126036 A1 | 9/2002 | Flaherty et al. |
| 2002/0128594 A1 | 9/2002 | Das et al. |
| 2002/0130042 A1 | 9/2002 | Moerman et al. |
| 2002/0133378 A1 | 9/2002 | Mault et al. |
| 2002/0147135 A1 | 10/2002 | Schnell |
| 2002/0161286 A1 | 10/2002 | Gerber et al. |
| 2002/0161288 A1 | 10/2002 | Shin et al. |
| 2002/0169394 A1 | 11/2002 | Eppstein et al. |
| 2002/0169635 A1 | 11/2002 | Shillingburg |
| 2002/0177764 A1 | 11/2002 | Sohrab |
| 2002/0193679 A1 | 12/2002 | Malave et al. |
| 2003/0004403 A1 | 1/2003 | Drinan et al. |
| 2003/0023182 A1 | 1/2003 | Mault et al. |
| 2003/0023317 A1 | 1/2003 | Brauker et al. |
| 2003/0028089 A1 | 2/2003 | Galley et al. |
| 2003/0028120 A1 | 2/2003 | Mault et al. |
| 2003/0032077 A1 | 2/2003 | Itoh et al. |
| 2003/0032867 A1 | 2/2003 | Crothall et al. |
| 2003/0032868 A1 | 2/2003 | Graskov et al. |
| 2003/0032874 A1 | 2/2003 | Rhodes et al. |
| 2003/0040683 A1 | 2/2003 | Rule et al. |
| 2003/0042137 A1 | 3/2003 | Mao et al. |
| 2003/0050537 A1 | 3/2003 | Wessel |
| 2003/0050546 A1 | 3/2003 | Desai et al. |
| 2003/0065257 A1 | 4/2003 | Mault et al. |
| 2003/0065273 A1 | 4/2003 | Mault et al. |
| 2003/0065274 A1 | 4/2003 | Mault et al. |
| 2003/0065275 A1 | 4/2003 | Mault et al. |
| 2003/0065308 A1 | 4/2003 | Lebel et al. |
| 2003/0100040 A1 | 5/2003 | Bonnecaze et al. |
| 2003/0100821 A1 | 5/2003 | Heller et al. |
| 2003/0105407 A1 | 6/2003 | Pearce et al. |
| 2003/0108976 A1 | 6/2003 | Braig et al. |
| 2003/0122021 A1 | 7/2003 | McConnell et al. |
| 2003/0125612 A1 | 7/2003 | Fox et al. |
| 2003/0130616 A1 | 7/2003 | Steil et al. |
| 2003/0134347 A1 | 7/2003 | Heller et al. |
| 2003/0135100 A1 | 7/2003 | Kim et al. |
| 2003/0135333 A1 | 7/2003 | Aceti et al. |
| 2003/0146841 A1* | 8/2003 | Koenig .......... 340/576 |
| 2003/0153820 A1 | 8/2003 | Berner et al. |
| 2003/0153821 A1 | 8/2003 | Berner et al. |
| 2003/0158472 A1 | 8/2003 | Sohrab |
| 2003/0158707 A1 | 8/2003 | Doi |
| 2003/0168338 A1 | 9/2003 | Gao et al. |
| 2003/0175806 A1 | 9/2003 | Rule et al. |
| 2003/0176183 A1 | 9/2003 | Drucker et al. |
| 2003/0176933 A1 | 9/2003 | Lebel et al. |
| 2003/0181851 A1 | 9/2003 | Mann et al. |
| 2003/0181852 A1 | 9/2003 | Mann et al. |
| 2003/0187338 A1 | 10/2003 | Say et al. |
| 2003/0187525 A1 | 10/2003 | Mann et al. |
| 2003/0191376 A1 | 10/2003 | Samuels et al. |
| 2003/0191431 A1 | 10/2003 | Mann et al. |
| 2003/0195403 A1 | 10/2003 | Berner et al. |
| 2003/0195462 A1 | 10/2003 | Mann et al. |
| 2003/0199790 A1 | 10/2003 | Boecker et al. |
| 2003/0199791 A1 | 10/2003 | Boecker et al. |
| 2003/0199903 A1 | 10/2003 | Boecker et al. |
| 2003/0203498 A1 | 10/2003 | Neel et al. |
| 2003/0208110 A1 | 11/2003 | Mault et al. |
| 2003/0208113 A1 | 11/2003 | Mault et al. |
| 2003/0208133 A1 | 11/2003 | Mault |
| 2003/0208409 A1 | 11/2003 | Mault |
| 2003/0212317 A1 | 11/2003 | Kovatchev et al. |
| 2003/0212364 A1 | 11/2003 | Mann et al. |
| 2003/0212379 A1 | 11/2003 | Bylund et al. |
| 2003/0216630 A1 | 11/2003 | Jersey-Willuhn et al. |
| 2003/0217966 A1 | 11/2003 | Tapsak et al. |
| 2003/0226695 A1 | 12/2003 | Mault |
| 2003/0229514 A2 | 12/2003 | Brown |
| 2003/0232370 A1 | 12/2003 | Trifiro |
| 2003/0235817 A1 | 12/2003 | Bartkowiak et al. |
| 2004/0010207 A1 | 1/2004 | Flaherty et al. |
| 2004/0011671 A1 | 1/2004 | Shults et al. |
| 2004/0018486 A1 | 1/2004 | Dunn et al. |
| 2004/0039256 A1 | 2/2004 | Kawatahara et al. |
| 2004/0039298 A1 | 2/2004 | Abreu |
| 2004/0040840 A1 | 3/2004 | Mao et al. |
| 2004/0045879 A1 | 3/2004 | Shults et al. |
| 2004/0054263 A1 | 3/2004 | Moerman et al. |
| 2004/0059201 A1 | 3/2004 | Ginsberg |
| 2004/0064068 A1 | 4/2004 | DeNuzzio et al. |
| 2004/0069164 A1 | 4/2004 | Nakamura et al. |
| 2004/0072357 A1 | 4/2004 | Stiene et al. |
| 2004/0073095 A1 | 4/2004 | Causey, III et al. |
| 2004/0096959 A1 | 5/2004 | Stiene et al. |
| 2004/0106858 A1 | 6/2004 | Say et al. |
| 2004/0108226 A1 | 6/2004 | Polychronakos et al. |
| 2004/0122353 A1 | 6/2004 | Shahmirian et al. |
| 2004/0122489 A1 | 6/2004 | Mazar et al. |
| 2004/0122530 A1 | 6/2004 | Hansen et al. |
| 2004/0133164 A1 | 7/2004 | Funderburk et al. |
| 2004/0138588 A1 | 7/2004 | Saikley |
| 2004/0146909 A1 | 7/2004 | Duong et al. |
| 2004/0152622 A1 | 8/2004 | Keith et al. |
| 2004/0152961 A1* | 8/2004 | Carlson et al. .......... 128/904 |
| 2004/0153585 A1 | 8/2004 | Kawatahara et al. |
| 2004/0162473 A1 | 8/2004 | Sohrab |
| 2004/0164961 A1 | 8/2004 | Bal et al. |
| 2004/0167383 A1 | 8/2004 | Kim et al. |
| 2004/0167464 A1 | 8/2004 | Ireland et al. |
| 2004/0167801 A1 | 8/2004 | Say et al. |
| 2004/0171921 A1 | 9/2004 | Say et al. |
| 2004/0172284 A1 | 9/2004 | Sullivan et al. |
| 2004/0176672 A1 | 9/2004 | Silver et al. |
| 2004/0176913 A1 | 9/2004 | Kawatahara et al. |
| 2004/0186362 A1 | 9/2004 | Brauker et al. |
| 2004/0186365 A1 | 9/2004 | Jin et al. |
| 2004/0193025 A1 | 9/2004 | Steil et al. |
| 2004/0193090 A1 | 9/2004 | Lebel et al. |
| 2004/0197846 A1 | 10/2004 | Hockersmith et al. |
| 2004/0199059 A1 | 10/2004 | Brauker et al. |
| 2004/0202576 A1 | 10/2004 | Aceti et al. |
| 2004/0204687 A1 | 10/2004 | Mogensen et al. |
| 2004/0208780 A1 | 10/2004 | Faries, Jr. et al. |
| 2004/0225338 A1 | 11/2004 | Lebel et al. |
| 2004/0235446 A1 | 11/2004 | Flaherty et al. |
| 2004/0236200 A1 | 11/2004 | Say et al. |
| 2004/0248204 A1 | 12/2004 | Moerman |
| 2004/0249250 A1 | 12/2004 | McGee et al. |
| 2004/0249253 A1 | 12/2004 | Racchini et al. |
| 2004/0249254 A1 | 12/2004 | Racchini et al. |
| 2004/0249999 A1 | 12/2004 | Connolly et al. |
| 2004/0253736 A1 | 12/2004 | Stout et al. |
| 2004/0254429 A1 | 12/2004 | Yang |
| 2004/0254433 A1 | 12/2004 | Bandis et al. |
| 2004/0254434 A1 | 12/2004 | Goodnow et al. |
| 2004/0260363 A1 | 12/2004 | Von Arx et al. |
| 2004/0263354 A1 | 12/2004 | Mann et al. |
| 2004/0267300 A1 | 12/2004 | Mace |
| 2005/0003470 A1* | 1/2005 | Nelson et al. .......... 600/365 |
| 2005/0004439 A1 | 1/2005 | Shin et al. |
| 2005/0004494 A1 | 1/2005 | Perez et al. |
| 2005/0010087 A1 | 1/2005 | Banet et al. |
| 2005/0010269 A1 | 1/2005 | Lebel et al. |
| 2005/0016276 A1 | 1/2005 | Guan et al. |
| 2005/0027177 A1 | 2/2005 | Shin et al. |
| 2005/0027179 A1 | 2/2005 | Berner et al. |
| 2005/0027180 A1 | 2/2005 | Goode, Jr. et al. |
| 2005/0027181 A1 | 2/2005 | Goode, Jr. et al. |
| 2005/0027462 A1 | 2/2005 | Goode, Jr. et al. |
| 2005/0027463 A1 | 2/2005 | Goode, Jr. et al. |
| 2005/0031689 A1 | 2/2005 | Shults et al. |
| 2005/0033132 A1 | 2/2005 | Shults et al. |
| 2005/0038332 A1 | 2/2005 | Saidara et al. |

| Publication No. | Date | Inventor |
|---|---|---|
| 2005/0038680 A1 | 2/2005 | McMahon |
| 2005/0043598 A1 | 2/2005 | Goode, Jr. et al. |
| 2005/0043894 A1 | 2/2005 | Fernandez |
| 2005/0049473 A1 | 3/2005 | Desai et al. |
| 2005/0054909 A1 | 3/2005 | Petisce et al. |
| 2005/0065464 A1 | 3/2005 | Talbot et al. |
| 2005/0090607 A1 | 4/2005 | Tapsak et al. |
| 2005/0096511 A1 | 5/2005 | Fox et al. |
| 2005/0096512 A1 | 5/2005 | Fox et al. |
| 2005/0112169 A1 | 5/2005 | Brauker et al. |
| 2005/0113653 A1 | 5/2005 | Fox et al. |
| 2005/0113657 A1 | 5/2005 | Alarcon et al. |
| 2005/0113658 A1 | 5/2005 | Jacobson et al. |
| 2005/0114068 A1 | 5/2005 | Chey et al. |
| 2005/0118726 A1 | 6/2005 | Schultz et al. |
| 2005/0121322 A1 | 6/2005 | Say et al. |
| 2005/0124873 A1 | 6/2005 | Shults et al. |
| 2005/0131346 A1 | 6/2005 | Douglas |
| 2005/0137471 A1 | 6/2005 | Haar et al. |
| 2005/0143635 A1 | 6/2005 | Kamath et al. |
| 2005/0143636 A1 | 6/2005 | Zhang et al. |
| 2005/0148003 A1 | 7/2005 | Keith et al. |
| 2005/0154271 A1 | 7/2005 | Rasdal et al. |
| 2005/0161346 A1 | 7/2005 | Simpson et al. |
| 2005/0171503 A1 | 8/2005 | Van Den Berghe et al. |
| 2005/0171513 A1 | 8/2005 | Mann et al. |
| 2005/0173245 A1 | 8/2005 | Feldman et al. |
| 2005/0176136 A1 | 8/2005 | Burd et al. |
| 2005/0177036 A1 | 8/2005 | Shults et al. |
| 2005/0177398 A1 | 8/2005 | Watanabe et al. |
| 2005/0181012 A1 | 8/2005 | Saint et al. |
| 2005/0182306 A1 | 8/2005 | Sloan |
| 2005/0182451 A1 | 8/2005 | Griffin et al. |
| 2005/0187720 A1 | 8/2005 | Goode, Jr. et al. |
| 2005/0192494 A1 | 9/2005 | Ginsberg |
| 2005/0192557 A1 | 9/2005 | Brauker et al. |
| 2005/0195930 A1 | 9/2005 | Spital et al. |
| 2005/0199494 A1 | 9/2005 | Say et al. |
| 2005/0203360 A1 | 9/2005 | Brauker et al. |
| 2005/0203707 A1 | 9/2005 | Tsutsui et al. |
| 2005/0214892 A1 | 9/2005 | Kovatchev et al. |
| 2005/0215871 A1 | 9/2005 | Feldman et al. |
| 2005/0215872 A1 | 9/2005 | Berner et al. |
| 2005/0239154 A1 | 10/2005 | Feldman et al. |
| 2005/0239156 A1 | 10/2005 | Drucker et al. |
| 2005/0241957 A1 | 11/2005 | Mao et al. |
| 2005/0245795 A1 | 11/2005 | Goode, Jr. et al. |
| 2005/0245799 A1 | 11/2005 | Brauker et al. |
| 2005/0245839 A1 | 11/2005 | Stivoric et al. |
| 2005/0245904 A1 | 11/2005 | Estes et al. |
| 2005/0251033 A1 | 11/2005 | Scarantino et al. |
| 2005/0251083 A1 | 11/2005 | Carr-Brendel et al. |
| 2005/0261660 A1 | 11/2005 | Choi |
| 2005/0267780 A1 | 12/2005 | Ray et al. |
| 2005/0271546 A1 | 12/2005 | Gerber et al. |
| 2005/0271547 A1 | 12/2005 | Gerber et al. |
| 2005/0272640 A1 | 12/2005 | Doyle, III et al. |
| 2005/0272985 A1 | 12/2005 | Kotulla et al. |
| 2005/0277164 A1 | 12/2005 | Drucker et al. |
| 2005/0287620 A1 | 12/2005 | Heller et al. |
| 2006/0001538 A1 | 1/2006 | Kraft et al. |
| 2006/0001550 A1 | 1/2006 | Mann et al. |
| 2006/0001551 A1 | 1/2006 | Kraft et al. |
| 2006/0003398 A1 | 1/2006 | Heller et al. |
| 2006/0004270 A1 | 1/2006 | Bedard et al. |
| 2006/0004271 A1 | 1/2006 | Peyser et al. |
| 2006/0007017 A1 | 1/2006 | Mann et al. |
| 2006/0015020 A1 | 1/2006 | Neale et al. |
| 2006/0015024 A1 | 1/2006 | Brister et al. |
| 2006/0016700 A1 | 1/2006 | Brister et al. |
| 2006/0019327 A1 | 1/2006 | Brister et al. |
| 2006/0020186 A1 | 1/2006 | Brister et al. |
| 2006/0020187 A1 | 1/2006 | Brister et al. |
| 2006/0020188 A1 | 1/2006 | Kamath et al. |
| 2006/0020189 A1 | 1/2006 | Brister et al. |
| 2006/0020190 A1 | 1/2006 | Kamath et al. |
| 2006/0020191 A1 | 1/2006 | Brister et al. |
| 2006/0020192 A1 | 1/2006 | Brister et al. |
| 2006/0025663 A1 | 2/2006 | Talbot et al. |
| 2006/0029177 A1 | 2/2006 | Cranford, Jr. et al. |
| 2006/0031094 A1 | 2/2006 | Cohen et al. |
| 2006/0036139 A1 | 2/2006 | Brister et al. |
| 2006/0036140 A1 | 2/2006 | Brister et al. |
| 2006/0036141 A1 | 2/2006 | Kamath et al. |
| 2006/0036142 A1 | 2/2006 | Brister et al. |
| 2006/0036143 A1 | 2/2006 | Brister et al. |
| 2006/0036144 A1 | 2/2006 | Brister et al. |
| 2006/0036145 A1 | 2/2006 | Brister et al. |
| 2006/0036187 A1 | 2/2006 | Vos et al. |
| 2006/0040402 A1 | 2/2006 | Brauker et al. |
| 2006/0052679 A1 | 3/2006 | Kotulla et al. |
| 2006/0058602 A1 | 3/2006 | Kwiatkowski et al. |
| 2006/0063218 A1 | 3/2006 | Bartkowiak et al. |
| 2006/0074564 A1 | 4/2006 | Bartowiak et al. |
| 2006/0142651 A1 | 6/2006 | Brister et al. |
| 2006/0155180 A1 | 7/2006 | Brister et al. |
| 2006/0166629 A1 | 7/2006 | Reggiardo |
| 2006/0173260 A1 | 8/2006 | Gaoni et al. |
| 2006/0173406 A1 | 8/2006 | Hayes et al. |
| 2006/0173444 A1 | 8/2006 | Choy et al. |
| 2006/0183985 A1 | 8/2006 | Brister et al. |
| 2006/0189863 A1 | 8/2006 | Peyser et al. |
| 2006/0195029 A1 | 8/2006 | Shults et al. |
| 2006/0200112 A1 | 9/2006 | Paul |
| 2006/0222566 A1 | 10/2006 | Brauker et al. |
| 2006/0224109 A1 | 10/2006 | Steil et al. |
| 2006/0224141 A1 | 10/2006 | Rush et al. |
| 2006/0226985 A1 | 10/2006 | Goodnow et al. |
| 2006/0229512 A1 | 10/2006 | Petisce et al. |
| 2006/0247508 A1 | 11/2006 | Fennell |
| 2006/0247985 A1 | 11/2006 | Liamos et al. |
| 2006/0258918 A1 | 11/2006 | Burd et al. |
| 2006/0258929 A1 | 11/2006 | Goode, Jr. et al. |
| 2006/0263763 A1 | 11/2006 | Simpson et al. |
| 2006/0272652 A1 | 12/2006 | Stocker et al. |
| 2006/0290496 A1 | 12/2006 | Peeters |
| 2007/0016381 A1 | 1/2007 | Kamath et al. |
| 2007/0027381 A1 | 2/2007 | Stafford |
| 2007/0033074 A1 | 2/2007 | Nitzan et al. |
| 2007/0060814 A1 | 3/2007 | Stafford |
| 2007/0066873 A1 | 3/2007 | Kamath et al. |
| 2007/0071681 A1 | 3/2007 | Gadkar et al. |
| 2007/0073129 A1 | 3/2007 | Shah et al. |
| 2007/0078320 A1 | 4/2007 | Stafford |
| 2007/0078321 A1 | 4/2007 | Mazza et al. |
| 2007/0078322 A1 | 4/2007 | Stafford |
| 2007/0078323 A1 | 4/2007 | Reggiardo et al. |
| 2007/0106135 A1 | 5/2007 | Sloan et al. |
| 2007/0124002 A1 | 5/2007 | Estes et al. |
| 2007/0149873 A1 | 6/2007 | Say et al. |
| 2007/0149874 A1 | 6/2007 | Say et al. |
| 2007/0149875 A1 | 6/2007 | Ouyang et al. |
| 2007/0151869 A1 | 7/2007 | Heller et al. |
| 2007/0161879 A1 | 7/2007 | Say et al. |
| 2007/0161880 A1 | 7/2007 | Say et al. |
| 2007/0163880 A1 | 7/2007 | Woo et al. |
| 2007/0168224 A1 | 7/2007 | Letzt et al. |
| 2007/0173706 A1 | 7/2007 | Neinast et al. |
| 2007/0173761 A1 | 7/2007 | Kanderian et al. |
| 2007/0179349 A1 | 8/2007 | Hoyme et al. |
| 2007/0179352 A1 | 8/2007 | Randlov et al. |
| 2007/0179370 A1 | 8/2007 | Say et al. |
| 2007/0179372 A1 | 8/2007 | Say et al. |
| 2007/0191699 A1 | 8/2007 | Say et al. |
| 2007/0191700 A1 | 8/2007 | Say et al. |
| 2007/0191701 A1 | 8/2007 | Feldman et al. |
| 2007/0203407 A1 | 8/2007 | Hoss et al. |
| 2007/0203408 A1 | 8/2007 | Say et al. |
| 2007/0203410 A1 | 8/2007 | Say et al. |
| 2007/0203411 A1 | 8/2007 | Say et al. |
| 2007/0203966 A1 | 8/2007 | Brauker et al. |
| 2007/0208247 A1 | 9/2007 | Say et al. |
| 2007/0213610 A1 | 9/2007 | Say et al. |
| 2007/0213657 A1 | 9/2007 | Jennewine et al. |
| 2007/0215491 A1 | 9/2007 | Heller et al. |
| 2007/0218097 A1 | 9/2007 | Heller et al. |
| 2007/0232877 A1 | 10/2007 | He |
| 2007/0235331 A1 | 10/2007 | Simpson et al. |

| | | | | | | |
|---|---|---|---|---|---|---|
| 2007/0244380 A1 | 10/2007 | Say et al. | | 2009/0006034 A1 | 1/2009 | Hayter et al. |
| 2007/0249919 A1 | 10/2007 | Say et al. | | 2009/0012379 A1 | 1/2009 | Goode et al. |
| 2007/0249920 A1 | 10/2007 | Say et al. | | 2009/0018424 A1 | 1/2009 | Kamath et al. |
| 2007/0249922 A1 | 10/2007 | Peyser et al. | | 2009/0030294 A1 | 1/2009 | Petisce et al. |
| 2008/0004515 A1 | 1/2008 | Jennewine et al. | | 2009/0033482 A1 | 2/2009 | Hayter et al. |
| 2008/0004601 A1 | 1/2008 | Jennewine et al. | | 2009/0036747 A1 | 2/2009 | Hayter et al. |
| 2008/0009692 A1 | 1/2008 | Stafford | | 2009/0036758 A1 | 2/2009 | Brauker et al. |
| 2008/0017522 A1 | 1/2008 | Heller et al. | | 2009/0036760 A1 | 2/2009 | Hayter |
| 2008/0021666 A1 | 1/2008 | Goode, Jr. et al. | | 2009/0036763 A1 | 2/2009 | Brauker et al. |
| 2008/0029391 A1 | 2/2008 | Mao et al. | | 2009/0043181 A1 | 2/2009 | Brauker et al. |
| 2008/0033254 A1 | 2/2008 | Kamath et al. | | 2009/0043182 A1 | 2/2009 | Brauker et al. |
| 2008/0039702 A1 | 2/2008 | Hayter et al. | | 2009/0043525 A1 | 2/2009 | Brauker et al. |
| 2008/0045824 A1 | 2/2008 | Tapsak et al. | | 2009/0043541 A1 | 2/2009 | Brauker et al. |
| 2008/0058625 A1 | 3/2008 | McGarraugh et al. | | 2009/0043542 A1 | 2/2009 | Brauker et al. |
| 2008/0064937 A1 | 3/2008 | McGarraugh et al. | | 2009/0045055 A1 | 2/2009 | Rhodes et al. |
| 2008/0071156 A1 | 3/2008 | Brister et al. | | 2009/0055149 A1 | 2/2009 | Hayter et al. |
| 2008/0071157 A1 | 3/2008 | McGarraugh et al. | | 2009/0062633 A1 | 3/2009 | Brauker et al. |
| 2008/0071158 A1 | 3/2008 | McGarraugh et al. | | 2009/0062635 A1 | 3/2009 | Brauker et al. |
| 2008/0081977 A1 | 4/2008 | Hayter et al. | | 2009/0062767 A1 | 3/2009 | VanAntwerp et al. |
| 2008/0083617 A1 | 4/2008 | Simpson et al. | | 2009/0063402 A1 | 3/2009 | Hayter |
| 2008/0086042 A1 | 4/2008 | Brister et al. | | 2009/0076356 A1 | 3/2009 | Simpson et al. |
| 2008/0086044 A1 | 4/2008 | Brister et al. | | 2009/0076360 A1 | 3/2009 | Brister et al. |
| 2008/0086273 A1 | 4/2008 | Shults et al. | | 2009/0076361 A1 | 3/2009 | Kamath et al. |
| 2008/0097289 A1 | 4/2008 | Steil et al. | | 2009/0099436 A1 | 4/2009 | Brister et al. |
| 2008/0108942 A1 | 5/2008 | Brister et al. | | 2009/0105636 A1 | 4/2009 | Hayter et al. |
| 2008/0154513 A1 | 6/2008 | Kovatchev et al. | | 2009/0124877 A1 | 5/2009 | Goode, Jr. et al. |
| 2008/0167543 A1 | 7/2008 | Say et al. | | 2009/0124878 A1 | 5/2009 | Goode et al. |
| 2008/0172205 A1 | 7/2008 | Breton et al. | | 2009/0124879 A1 | 5/2009 | Brister et al. |
| 2008/0183060 A1 | 7/2008 | Steil et al. | | 2009/0124964 A1 | 5/2009 | Leach et al. |
| 2008/0183061 A1 | 7/2008 | Goode et al. | | 2009/0131768 A1 | 5/2009 | Simpson et al. |
| 2008/0183399 A1 | 7/2008 | Goode et al. | | 2009/0131769 A1 | 5/2009 | Leach et al. |
| 2008/0188731 A1 | 8/2008 | Brister et al. | | 2009/0131776 A1 | 5/2009 | Simpson et al. |
| 2008/0188796 A1 | 8/2008 | Steil et al. | | 2009/0131777 A1 | 5/2009 | Simpson et al. |
| 2008/0189051 A1 | 8/2008 | Goode et al. | | 2009/0137886 A1 | 5/2009 | Shariati et al. |
| 2008/0194935 A1 | 8/2008 | Brister et al. | | 2009/0137887 A1 | 5/2009 | Shariati et al. |
| 2008/0194936 A1 | 8/2008 | Goode et al. | | 2009/0143659 A1 | 6/2009 | Li et al. |
| 2008/0194937 A1 | 8/2008 | Goode et al. | | 2009/0143660 A1 | 6/2009 | Brister et al. |
| 2008/0194938 A1 | 8/2008 | Brister et al. | | 2009/0149717 A1 | 6/2009 | Brauer et al. |
| 2008/0195232 A1 | 8/2008 | Carr-Brendel et al. | | 2009/0156919 A1 | 6/2009 | Brister et al. |
| 2008/0195967 A1 | 8/2008 | Goode et al. | | 2009/0156924 A1 | 6/2009 | Shariati et al. |
| 2008/0197024 A1 | 8/2008 | Simpson et al. | | 2009/0163790 A1 | 6/2009 | Brister et al. |
| 2008/0200788 A1 | 8/2008 | Brister et al. | | 2009/0163791 A1 | 6/2009 | Brister et al. |
| 2008/0200789 A1 | 8/2008 | Brister et al. | | 2009/0164190 A1 | 6/2009 | Hayter |
| 2008/0200791 A1 | 8/2008 | Simpson et al. | | 2009/0164239 A1 | 6/2009 | Hayter et al. |
| 2008/0208025 A1 | 8/2008 | Shults et al. | | 2009/0164251 A1 | 6/2009 | Hayter |
| 2008/0208113 A1 | 8/2008 | Damiano et al. | | 2009/0178459 A1 | 7/2009 | Li et al. |
| 2008/0214915 A1 | 9/2008 | Brister et al. | | 2009/0182217 A1 | 7/2009 | Li et al. |
| 2008/0214918 A1 | 9/2008 | Brister et al. | | 2009/0192366 A1 | 7/2009 | Mensinger et al. |
| 2008/0228051 A1 | 9/2008 | Shults et al. | | 2009/0192380 A1 | 7/2009 | Shariati et al. |
| 2008/0228054 A1 | 9/2008 | Shults et al. | | 2009/0192722 A1 | 7/2009 | Shariati et al. |
| 2008/0242961 A1 | 10/2008 | Brister et al. | | 2009/0192724 A1 | 7/2009 | Brauker et al. |
| 2008/0255434 A1 | 10/2008 | Hayter et al. | | 2009/0192745 A1 | 7/2009 | Kamath et al. |
| 2008/0255437 A1 | 10/2008 | Hayter | | 2009/0192751 A1 | 7/2009 | Kamath et al. |
| 2008/0255808 A1 | 10/2008 | Hayter | | 2009/0198118 A1 | 8/2009 | Hayter et al. |
| 2008/0256048 A1 | 10/2008 | Hayter | | 2009/0203981 A1 | 8/2009 | Brauker et al. |
| 2008/0262469 A1 | 10/2008 | Brister et al. | | 2009/0204341 A1 | 8/2009 | Brauker et al. |
| 2008/0275313 A1 | 11/2008 | Brister et al. | | 2009/0216103 A1 | 8/2009 | Brister et al. |
| 2008/0287761 A1 | 11/2008 | Hayter | | 2009/0240120 A1 | 9/2009 | Mensinger et al. |
| 2008/0287762 A1 | 11/2008 | Hayter | | 2009/0240128 A1 | 9/2009 | Mensinger et al. |
| 2008/0287763 A1 | 11/2008 | Hayter | | 2009/0240193 A1 | 9/2009 | Mensinger et al. |
| 2008/0287764 A1 | 11/2008 | Rasdal et al. | | 2009/0242399 A1 | 10/2009 | Kamath et al. |
| 2008/0287765 A1 | 11/2008 | Rasdal et al. | | 2009/0242425 A1 | 10/2009 | Kamath et al. |
| 2008/0287766 A1 | 11/2008 | Rasdal et al. | | 2009/0247855 A1 | 10/2009 | Boock et al. |
| 2008/0288180 A1 | 11/2008 | Hayter | | 2009/0247856 A1 | 10/2009 | Boock et al. |
| 2008/0288204 A1 | 11/2008 | Hayter et al. | | 2009/0287073 A1 | 11/2009 | Boock et al. |
| 2008/0296155 A1 | 12/2008 | Shults et al. | | 2009/0287074 A1 | 11/2009 | Shults et al. |
| 2008/0300919 A1 | 12/2008 | Charlton et al. | | 2009/0299155 A1 | 12/2009 | Yang et al. |
| 2008/0300920 A1 | 12/2008 | Brown et al. | | 2009/0299156 A1 | 12/2009 | Simpson et al. |
| 2008/0301158 A1 | 12/2008 | Brown et al. | | 2009/0299162 A1 | 12/2009 | Brauker et al. |
| 2008/0301665 A1 | 12/2008 | Charlton et al. | | 2009/0299276 A1 | 12/2009 | Brauker et al. |
| 2008/0306368 A1 | 12/2008 | Goode et al. | | 2010/0010324 A1 | 1/2010 | Brauker et al. |
| 2008/0306434 A1 | 12/2008 | Dobbles et al. | | 2010/0010331 A1 | 1/2010 | Brauker et al. |
| 2008/0306435 A1 | 12/2008 | Kamath et al. | | 2010/0010332 A1 | 1/2010 | Brauker et al. |
| 2008/0306444 A1 | 12/2008 | Brister et al. | | 2010/0016687 A1 | 1/2010 | Brauker et al. |
| 2008/0312841 A1 | 12/2008 | Hayter | | 2010/0016698 A1 | 1/2010 | Rasdal et al. |
| 2008/0312842 A1 | 12/2008 | Hayter | | 2010/0022855 A1 | 1/2010 | Brauker et al. |
| 2008/0312844 A1 | 12/2008 | Hayter et al. | | 2010/0030038 A1 | 2/2010 | Brauker et al. |
| 2008/0312845 A1 | 12/2008 | Hayter et al. | | 2010/0030053 A1 | 2/2010 | Goode, Jr. et al. |
| 2009/0005665 A1 | 1/2009 | Hayter et al. | | 2010/0030484 A1 | 2/2010 | Brauker et al. |

| | | | | | | |
|---|---|---|---|---|---|---|
| 2010/0030485 A1 | 2/2010 | Brauker et al. | | WO | WO 86/00513 | 1/1986 |
| 2010/0036215 A1 | 2/2010 | Goode, Jr. et al. | | WO | WO-87/00513 | 1/1987 |
| 2010/0036216 A1 | 2/2010 | Goode, Jr. et al. | | WO | WO 87/06040 | 10/1987 |
| 2010/0036222 A1 | 2/2010 | Goode, Jr. et al. | | WO | WO 89/02246 | 3/1989 |
| 2010/0036223 A1 | 2/2010 | Goode, Jr. et al. | | WO | WO-89/05119 | 6/1989 |
| 2010/0036225 A1 | 2/2010 | Goode, Jr. et al. | | WO | WO-89/08713 | 9/1989 |
| 2010/0041971 A1 | 2/2010 | Goode, Jr. et al. | | WO | WO 90/00367 | 1/1990 |
| 2010/0045465 A1 | 2/2010 | Brauker et al. | | WO | WO-90/05300 | 5/1990 |
| 2010/0049024 A1 | 2/2010 | Saint et al. | | WO | WO-90/05910 | 5/1990 |
| 2010/0057040 A1 | 3/2010 | Hayter | | WO | WO-91/01680 | 2/1991 |
| 2010/0057041 A1 | 3/2010 | Hayter | | WO | WO-91/04704 | 4/1991 |
| 2010/0057042 A1 | 3/2010 | Hayter | | WO | WO-91/15993 | 10/1991 |
| 2010/0057044 A1 | 3/2010 | Hayter | | WO | WO-92/01947 | 2/1992 |
| 2010/0057057 A1 | 3/2010 | Hayter et al. | | WO | WO-92/13271 | 8/1992 |
| 2010/0063373 A1 | 3/2010 | Kamath et al. | | WO | WO-94/20602 | 9/1994 |
| 2010/0076283 A1 | 3/2010 | Simpson et al. | | WO | WO-94/27140 | 11/1994 |
| 2010/0081908 A1 | 4/2010 | Dobbles et al. | | WO | WO 95/06240 | 3/1995 |
| 2010/0081910 A1 | 4/2010 | Brister et al. | | WO | WO 96/07908 | 3/1996 |
| 2010/0087724 A1 | 4/2010 | Brauker et al. | | WO | WO-96/25089 | 8/1996 |
| 2010/0096259 A1 | 4/2010 | Zhang et al. | | WO | WO-96/30431 | 10/1996 |
| 2010/0099970 A1 | 4/2010 | Shults et al. | | WO | WO-96/35370 | 11/1996 |
| 2010/0099971 A1 | 4/2010 | Shults et al. | | WO | WO-97/02847 | 1/1997 |
| 2010/0119693 A1 | 5/2010 | Tapsak et al. | | WO | WO-97/19344 | 5/1997 |
| 2010/0121169 A1 | 5/2010 | Petisce et al. | | WO | WO 97/20207 | 6/1997 |
| | | | | WO | WO 97/41421 | 11/1997 |
| FOREIGN PATENT DOCUMENTS | | | | WO | WO-97/42882 | 11/1997 |
| | | | | WO | WO-97/42883 | 11/1997 |
| EP | 0010375 | 4/1980 | | WO | WO-97/42886 | 11/1997 |
| EP | 1 579 690 | 11/1980 | | WO | WO-97/42888 | 11/1997 |
| EP | 0026995 | 4/1981 | | WO | WO-97/43962 | 11/1997 |
| EP | 0048090 | 3/1982 | | WO | WO 97/46868 | 12/1997 |
| EP | 0078636 | 5/1983 | | WO | WO 98/09167 | 3/1998 |
| EP | 0080304 | 6/1983 | | WO | WO-98/09167 | 3/1998 |
| EP | 0098592 | 1/1984 | | WO | WO 98/24366 | 6/1998 |
| EP | 0125139 | 11/1984 | | WO | WO-98/35053 | 8/1998 |
| EP | 0127958 | 12/1984 | | WO | WO 98/52045 | 11/1998 |
| EP | 0136362 | 4/1985 | | WO | WO-98/52293 | 11/1998 |
| EP | 0170375 | 2/1986 | | WO | WO 99/05966 | 2/1999 |
| EP | 0177743 | 4/1986 | | WO | WO 99/32883 | 7/1999 |
| EP | 0184909 | 6/1986 | | WO | WO-99/56613 | 11/1999 |
| EP | 0206218 | 12/1986 | | WO | WO 00/13580 | 3/2000 |
| EP | 0230472 | 8/1987 | | WO | WO-00/18294 | 4/2000 |
| EP | 0241309 | 10/1987 | | WO | WO-00/19887 | 4/2000 |
| EP | 0245073 | 11/1987 | | WO | WO 00/20626 | 4/2000 |
| EP | 0255291 | 2/1988 | | WO | WO 00/33065 | 6/2000 |
| EP | 0278647 | 8/1988 | | WO | WO-00/49940 | 8/2000 |
| EP | 0320109 | 6/1989 | | WO | WO-00/59370 | 10/2000 |
| EP | 0353328 | 2/1990 | | WO | WO-00/62664 | 10/2000 |
| EP | 0359831 | 3/1990 | | WO | WO-00/62665 | 10/2000 |
| EP | 0368209 | 5/1990 | | WO | WO 00/78210 | 12/2000 |
| EP | 0390390 | 10/1990 | | WO | WO-00/78992 | 12/2000 |
| EP | 0396788 | 11/1990 | | WO | WO 01/24038 | 4/2001 |
| EP | 0400918 | 12/1990 | | WO | WO 01/33216 | 5/2001 |
| EP | 0453283 | 10/1991 | | WO | WO 01/52727 | 7/2001 |
| EP | 0470290 | 2/1992 | | WO | WO-01/52935 | 7/2001 |
| EP | 0 504 835 A2 | 9/1992 | | WO | WO-01/54753 | 8/2001 |
| EP | 0286118 | 1/1995 | | WO | WO 01/57238 | 8/2001 |
| EP | 0 653 718 A2 | 5/1995 | | WO | WO 01/57239 | 8/2001 |
| EP | 0 800 082 A2 | 10/1997 | | WO | WO 01/67009 | 9/2001 |
| EP | 0 800 082 A3 | 10/1997 | | WO | WO-02/13686 | 2/2002 |
| EP | 0 880 936 A3 | 12/1998 | | WO | WO-02/16905 | 2/2002 |
| EP | 0 970 655 A1 | 1/2000 | | WO | WO-02/17210 | 2/2002 |
| EP | 1034734 | 9/2000 | | WO | WO 02/078512 A2 | 10/2002 |
| EP | 1048264 | 11/2000 | | WO | WO 02/078512 A3 | 10/2002 |
| EP | 1445746 | 8/2004 | | WO | WO-03/036583 | 5/2003 |
| GB | 1394171 | 5/1975 | | WO | WO-03/076893 | 9/2003 |
| GB | 1 579 690 A | 11/1980 | | WO | WO-03/082091 | 10/2003 |
| GB | 1579690 | 11/1980 | | WO | WO-03/085372 | 10/2003 |
| GB | 1599241 | 9/1981 | | WO | WO-2004/061420 | 7/2004 |
| GB | 2073891 | 10/1981 | | WO | WO-2005/041766 | 5/2005 |
| GB | 2154003 | 8/1985 | | WO | WO-2005/089103 | 9/2005 |
| GB | 2204408 | 11/1988 | | WO | WO-2006/024671 | 3/2006 |
| GB | 2 225 637 A | 6/1990 | | WO | WO-2006/037109 | 4/2006 |
| GB | 2225637 | 6/1990 | | WO | WO-2006/079114 | 7/2006 |
| GB | 2254436 | 10/1992 | | WO | WO-2006/118947 | 11/2006 |
| GB | 2 194 892 A | 3/1998 | | WO | WO-2006/119084 | 11/2006 |
| JP | 8-154903 | 6/1996 | | WO | WO-2007/002189 | 1/2007 |
| JP | 2000-000231 | 1/2000 | | WO | WO-2007/016399 | 2/2007 |
| JP | 2000-116628 | 4/2000 | | WO | WO-2007/027381 | 3/2007 |
| WO | WO-85/05119 | 11/1985 | | | | |

| | | |
|---|---|---|
| WO | WO-2007/027788 | 3/2007 |
| WO | WO-2007/041069 | 4/2007 |
| WO | WO-2007/041070 | 4/2007 |
| WO | WO-2007/041072 | 4/2007 |
| WO | WO-2007/041248 | 4/2007 |
| WO | WO-2007/056638 | 5/2007 |
| WO | WO-2007/101223 | 9/2007 |
| WO | WO-2007/101260 | 9/2007 |
| WO | WO-2007/120363 | 10/2007 |
| WO | WO-2007/126444 | 11/2007 |
| WO | WO-2007/053832 | 12/2007 |
| WO | WO-2007/143225 | 12/2007 |
| WO | WO-2008/003003 | 1/2008 |
| WO | WO-2008/005780 | 1/2008 |
| WO | WO-2008/021913 | 2/2008 |
| WO | WO-2008/042760 | 4/2008 |
| WO | WO-2008/128210 | 10/2008 |
| WO | WO-2008/130896 | 10/2008 |
| WO | WO-2008/130897 | 10/2008 |
| WO | WO-2008/130898 | 10/2008 |
| WO | WO-2008/143943 | 11/2008 |
| WO | WO-2008/150428 | 12/2008 |
| WO | WO-2008/153825 | 12/2008 |
| WO | WO-2009/018058 | 2/2009 |
| WO | WO-2009/075697 | 6/2009 |
| WO | WO-2009/086216 | 7/2009 |
| WO | WO-2009/096992 | 8/2009 |
| WO | WO-2009/097594 | 8/2009 |

OTHER PUBLICATIONS

Abstract of Japanese Publication No. JP-55-010581, Published Jan. 5, 1980.
Abstract of Japanese Publication No. JP-55-010583, Published Jan. 5, 1980.
Abstract of Japanese Publication No. JP-55-010584, Published Jan. 5, 1980.
Albery, W. J., et al., "Amperometric Enzyme Electrodes Part II: Conducting Salts as Electrode Materials for the Oxidation of Glucose Oxidase", *Journal of ElectroAnalytical Chemistry*, vol. 194, 1985, pp. 223-235.
Albery, W. J., et al., "Amperometric Enzyme Electrodes", *Philosophical Transactions of The Royal Society of London*, vol. 316, 1987, pp. 107-119. .
Alcock, S. J., et al., "Continuous Analyte Monitoring to Aid Clinical Practice", *IEEE Engineering in Medicine and Biology Magazine*, 1994, pp. 319-325.
Anderson, L. B., et al., "Thin-Layer Electrochemistry: Steady-State Methods of Studying Rate Processes", *Journal of ElectroAnalytical Chemistry*, vol. 10, 1965, pp. 295-305.
Armour, J. C., et al., "Application of Chronic Intravascular Blood Glucose Sensor in Dogs", *Diabetes*, vol. 39, 1990, pp. 1519-1526.
Bartlett, P. N., et al., "Covalent Binding of Electron Relays to Glucose Oxidase", *Journal of the Chemical Society, Chemical Communications*, 1987, pp. 1603-1604.
Bartlett, P. N., et al., "Modification of Glucose Oxidase by Tetrathiafulvalene", *Journal of the Chemical Society, Chemical Communications*, 1990, pp. 1135-1136.
Bartlett, P. N., et al., "Strategies for the Development of Amperometric Enzyme Electrodes", *Biosensors*, vol. 3, 1987/88, pp. 359-379.
Bennion, N., et al., "Alternate Site Glucose Testing: A Crossover Design", *Diabetes Technology & Therapeutics*, vol. 4, No. 1, 2002, pp. 25-33.
Bindra, D. S., et al., "Design and in Vitro Studies of a Needle-Type Glucose Sensor for Subcutaneous Monitoring", *Analytical Chemistry*, vol. 63, No. 17, 1991, pp. 1692-1696.
Blank, T. B., et al., "Clinical Results From a Non-Invasive Blood Glucose Monitor", *Optical Diagnostics and Sensing of Biological Fluids and Glucose and Cholesterol Monitoring II, Proceedings of SPIE*, vol. 4624, 2002, pp. 1-10.
Bobbioni-Harsch, E., et al., "Lifespan of Subcutaneous Glucose Sensors and Their Performances During Dynamic Glycaemia Changes in Rats", *Journal of Biomedical Engineering*, vol. 15, 1993, pp. 457-463.

Boedeker Plastics, Inc., "Polyethylene Specifications", *Web Page of Boedeker.com*, 2007, pp. 1-3.
Brandt, J., et al., "Covalent Attachment of Proteins to Polysaccharide Carriers by Means of Benzoquinone", *Biochimica et Biophysica Acta*, vol. 386, 1975, pp. 196-202.
Brooks, S. L., et al., "Development of an On-Line Glucose Sensor for Fermentation Monitoring", *Biosensors*, vol. 3, 1987/88, pp. 45-56.
Brownlee, M., et al., "A Glucose-Controlled Insulin-Delivery System: Semisynthetic Insulin Bound to Lectin", *Science*, vol. 206, 1979, 1190-1191.
Cass, A. E., et al., "Ferricinum Ion As an Electron Acceptor for Oxido-Reductases", *Journal of ElectroAnalytical Chemistry*, vol. 190, 1985, pp. 117-127.
Cass, A. E., et al., "Ferrocene-Medicated Enzyme Electrode for Amperometric Determination of Glucose", *Analytical Chemistry*, vol. 56, No. 4, 1984, 667-671.
Castner, J. F., et al., "Mass Transport and Reaction Kinetic Parameters Determined Electrochemically for Immobilized Glucose Oxidase", *Biochemistry*, vol. 23 No. 10, 1984, 2203-2210.
Claremont, D. J., et al., "Biosensors for Continuous in Vivo Glucose Monitoring", *Proceedings of the Annual International Conference of the IEEE Engineering in Medicine and Biology Society*, vol. 10, 1988.
Clark Jr., L. C., et al., "Differential Anodic Enzyme Polarography for the Measurement of Glucose", *Oxygen Transport to Tissue: Instrumentation, Methods, and Physiology*, 1973, pp. 127-133.
Clark Jr., L. C., et al., "Electrode Systems for Continuous Monitoring in Cardiovascular Surgery", *Annals New York Academy of Sciences*, 1962, pp. 29-45.
Clark Jr., L. C., et al., "Long-term Stability of Electroenzymatic Glucose Sensors Implanted in Mice", *American Society of Artificial Internal Organs Transactions*, vol. XXXIV, 1988, pp. 259-265.
Clarke, W. L., et al., "Evaluating Clinical Accuracy of Systems for Self-Monitoring of Blood Glucose", *Diabetes Care*, vol. 10, No. 5, 1987, pp. 622-628.
Csoregi, E., et al., "Design and Optimization of a Selective Subcutaneously Implantable Glucose Electrode Based on 'Wired' Glucose Oxidase", *Analytical Chemistry*, vol. 67, No. 7, 1995, pp. 1240-1244.
Csoregi, E., et al., "Design, Characterization, and One-Point in Vivo Calibration of a Subcutaneously Implanted Glucose Electrode", *Analytical Chemistry*, vol. 66 No. 19, 1994, pp. 3131-3138.
Csoregi, E., et al., "On-Line Glucose Monitoring by Using Microdialysis Sampling and Amperometric Detection Based on 'Wired' Glucose Oxidase in Carbon Paste", *Mikrochimica Acta*, vol. 121, 1995, pp. 31-40.
Dai, W. S., et al., "Hydrogel Membranes with Mesh Size Asymmetry Based on the Gradient Crosslinking of Poly(vinyl alcohol)," *Journal of Membrane Science*, vol. 156, 1999, pp. 67-79.
Davis, G., "Electrochemical Techniques for the Development of Amperometric Biosensors", *Biosensors*, vol. 1, 1985, pp. 161-178.
Degani, Y., et al., "Direct Electrical Communication Between Chemically Modified Enzymes and Metal Electrodes. 1. Electron Transfer from Glucose Oxidase to Metal Electrodes via Electron Relays, Bound Covalently to the Enzyme", *The Journal of Physical Chemistry*, vol. 91, No. 6, 1987, pp. 1285-1289.
Degani, Y., et al., "Direct Electrical Communication Between Chemically Modified Enzymes and Metal Electrodes. 2. Methods for Bonding Electron-Transfer Relays to Glucose Oxidase and D-Amino-Acid Oxidase", *Journal of the American Chemical Society*, vol. 110, No. 8, 1988, pp. 2615-2620.
Degani, Y., et al., "Electrical Communication Between Redox Centers of Glucose Oxidase and Electrodes via Electrostatically and Covalently Bound Redox Polymers", *Journal of the American Chemical Society*, vol. 111, 1989, pp. 2357-2358.
Denisevich, P., et al., "Unidirectional Current Flow and Charge State Trapping at Redox Polymer Interfaces on Bilayer Electrodes: Principles, Experimental Demonstration, and Theory", *Journal of the American Chemical Society*, vol. 103, 1981, pp. 4727-4737.
Dicks, J. M., et al., "Ferrocene Modified Polypyrrole with Immobilised Glucose Oxidase and its Application in Amperometric Glucose Microbiosensors", *Annales de Biologie Clinique*, vol. 47, 1989, pp. 607-619.

Ellis, C. D., et al., "Selectivity and Directed Charge Transfer through an Electroactive Metallopolymer Film", *Journal of the American Chemical Society*, vol. 103, No. 25, 1981, pp. 7480-7483.

Engstrom, R. C., "Electrochemical Pretreatment of Glassy Carbon Electrodes", *Analytical Chemistry*, vol. 54, No. 13, 1982, pp. 2310-2314.

Engstrom, R. C., et al., "Characterization of Electrochemically Pretreated Glassy Carbon Electrodes", *Analytical Chemistry*, vol. 56, No. 2, 1984, pp. 136-141.

Feldman, B., et al., "A Continuous Glucose Sensor Based on Wired Enzyme™ Technology—Results from a 3-Day Trial in Patients with Type 1 Diabetes", *Diabetes Technology & Therapeutics*, vol. 5, No. 5, 2003, pp. 769-779.

Feldman, B., et al., "Correlation of Glucose Concentrations in Interstitial Fluid and Venous Blood During Periods of Rapid Glucose Change", *Abbott Diabetes Care, Inc. Freestyle Navigator Continuous Glucose Monitor Pamphlet*, 2004.

Feldman, B., et al., "Electron Transfer Kinetics at Redox Polymer/Solution Interfaces Using Microelectrodes and Twin Electrode Thin Layer Cells", *Journal of ElectroAnalytical Chemistry*, vol. 194, 1985, pp. 63-81.

Fischer, H., et al., "Intramolecular Electron Transfer Medicated by 4,4"-Bypyridine and Related Bridging Groups", *Journal of the American Chemical Society*, vol. 98, No. 18, 1976, pp. 5512-5517.

Flentge, F., et al., "An Enzyme-Reactor for Electrochemical Monitoring of Choline and Acetylcholine: Applications in High-Performance Liquid Chromatography, Bran Tissue, Microdialysis and Cerebrospinal Fluid," *Analytical Biochemistry*, vol. 204, 1992, pp. 305-310.

Foulds, N. C., et al., "Enzyme Entrapment in Electrically Conducting Polymers: Immobilisation of Glucose Oxidase in Polypyrrole and its Application in Amperometric Glucose Sensors", *Journal of the Chemical Society, Faraday Transactions 1*, vol. 82, 1986, pp. 1259-1264.

Foulds, N. C., et al, "Immobilization of Glucose Oxidase in Ferrocene-Modified Pyrrole Polymers", *Analytical Chemistry*, vol. 60, No. 22, 1988, pp. 2473-2478.

Frew, J. E., et al., "Electron-Transfer Biosensors", *Philosophical Transactions of the Royal Society of London*, vol. 316, 1987, pp. 95-106.

Godsland, I. F., et al., "Maximizing the Success Rate of Minimal Model Insulin Sensitivity Measurement in Humans: The Importance of Basal Glucose Levels," *Clinical Science*, vol. 101, 2001, pp. 1-9.

Gorton, L., et al., "Selective Detection in Flow Analysis Based on the Combination of Immobilized Enzymes and Chemically Modified Electrodes", *Analytica Chimica Acta*, vol. 250, 1991, pp. 203-248.

Graham, N. B., "Poly(ethylene oxide) and Related Hydrogels," *Hydrogels in Medicine and Pharmacy*, vol. II: Polymers, Chapter 4, 1987, pp. 95-113.

Gregg, B. A., et al., "Cross-Linked Redox Gels Containing Glucose Oxidase for Amperometric Bionsensor Applications", *Analytical Chemistry*, vol. 62, No. 3, 1990, pp. 258-263.

Gregg, B. A., et al., "Redox Polymer Films Containing Enzymes. 1. A Redox-Conducting Epoxy Cement: Synthesis, Characterization, and Electrocatalytic Oxidation of Hydroquinone", *Journal of Physical Chemistry*, vol. 95, No. 15, 1991, 5970-5975.

Hale, P. D., et al., "A New Class of Amperometric Biosensor Incorporating a Polymeric Electron-Transfer Mediator", *Journal of the American Chemical Society*, vol. 111, No. 9, 1989, pp. 3482-3484.

Harrison, D. J., et al., "Characterization of Perfluorosulfonic Acid Polymer Coated Enzyme Electrodes and a Miniatureized Integrated Potentiostat for Glucose Analysis in Whole Blood", *Analytical Chemistry*, vol. 60, No. 19, 1988, pp. 2002-2007.

Hawkridge, F. M., et al., "Indirect Coulometric Titration of Biological Electron Transport Components", *Analytical Chemistry*, vol. 45, No. 7, 1973, pp. 1021-1027.

Heller, A., "Electrical Connection Enzyme Redox Centers to Electrodes", *Journal of Physical Chemistry*, vol. 96, No. 9, 1990, pp. 3579-3587.

Heller, A., "Electrical Wiring of Redox Enzymes", *Accounts of Chemical Research* vol. 23, No. 5, 1990, 128-134.

Heller, A., et al., "Amperometric Biosensors Based on Three-Dimensional Hydrogel-Forming Epoxy Networks", *Sensors and Actuators B*, vol. 13-14, 1993, pp. 180-183.

Ianniello, R. M., et al., "Differential Pulse Voltammetric Study of Direct Electron Transfer in Glucose Oxidase Chemically Modified Graphite Electrodes", *Analytical Chemistry*, vol. 54, No. 7, 1982, pp. 1098-1101.

Ianniello, R. M., et al., "Immobilized Enzyme Chemically Modified Electrode as an Amperometric Sensor", *Analytical Chemistry*, vol. 53, No. 13, 1981, pp. 2090-2095.

Ikeda, T., et al., "Glucose Oxidase-Immobilized Benzoquinone-Carbon Paste Electrode as a Glucose Sensor", *Agricultural and Biological Chemistry*, vol. 49, No. 2, 1985, pp. 541-543.

Ikeda, T., et al., "Kinetics of Outer-Sphere Electron Transfers Between Metal Complexes in Solutions and Polymeric Films on Modified Electrodes", *Journal of the American Chemical Society*, vol. 103, No. 25, 1981, pp. 7422-7425.

Isermann, R., "Supervision, Fault-Detection and Fault-Diagnosis Methods—An Introduction", *Control Engineering Practice*, vol. 5, No. 5, 1997, pp. 639-652.

Isermann, R., et al., "Trends in the Application of Model-Based Fault Detection and Diagnosis of Technical Processes", *Control Engineering Practice*, vol. 5, No. 5, 1997, pp. 709-719.

Johnson, J. M., et al., "Potential-Dependent Enzymatic Activity in an Enzyme Thin-Layer Cell", *Analytical Chemistry*, vol. 54, No. 8, 1982, pp. 1377-1383.

Johnson, K. W., "Reproducible Electrodeposition of Biomolecules for the Fabrication of Miniature Electroenzymatic Biosensors", *Sensors and Actuators B*, vol. 5, 1991, pp. 85-89.

Johnson, K. W., et al., "In vivo Evaluation of an Electroenzymatic Glucose Sensor Implanted in Subcutaneous Tissue", *Biosensors & Bioelectronics*, vol. 7, 1992, pp. 709-714.

Johnson, P. C., "Peripheral Circulation", *John Wiley & Sons*, 1978, pp. 198.

Jonsson, G., et al., "An Amperometric Glucose Sensor Made by Modification of a Graphite Electrode Surface With Immobilized Glucose Oxidase and Adsorbed Mediator", *Biosensors*, vol. 1, 1985, pp. 355-368.

Josowicz, M., et al., "Electrochemical Pretreatment of Thin Film Platinum Electrodes", *Journal of the Electrochemical Society*, vol. 135 No. 1, 1988, pp. 112-115.

Jungheim, K., et al., "How Rapid Does Glucose Concentration Change in Daily Life of Patients with Type 1 Diabetes?", 2002, pp. 250.

Jungheim, K., et al., "Risky Delay of Hypoglycemia Detection by Glucose Monitoring at the Arm", *Diabetes Care*, vol. 24, No. 7, 2001, pp. 1303-1304.

Kaplan, S. M., "Wiley Electrical and Electronics Engineering Dictionary", *IEEE Press*, 2004, pp. 141, 142, 548, 549.

Katakis, I., et al., "Electrostatic Control of the Electron Transfer Enabling Binding of Recombinant Glucose Oxidase and Redox Polyelectrolytes", *Journal of the American Chemical Society*, vol. 116, No. 8, 1994, pp. 3617-3618.

Katakis, I., et al., "L-α-Glycerophosphate and L-Lactate Electrodes Based on the Electrochemical 'Wiring' of Oxidases", *Analytical Chemistry*, vol. 64, No. 9, 1992, pp. 1008-1013.

Kemp, G. J., "Theoretical Aspects of One-Point Calibration: Causes and Effects of Some Potential Errors, and Their Dependence on Concentration," *Clinical Chemistry*, vol. 30, No. 7, 1984, pp. 1163-1167.

Kenausis, G., et al., "'Wiring' of Glucose Oxidase and Lactate Oxidase Within a Hydrogel Made with Poly(vinyl pyridine) complexed with $[Os(4,4"-dimethoxy-2,2"-bipyridine)_2Cl]^{+/2+}$", *Journal of the Chemical Society, Faraday Transactions*, vol. 92, No. 20, 1996, pp. 4131-4136.

Kerner, W., et al., "The Function of a Hydrogen Peroxide-Detecting Electroenzymatic Glucose Electrode is Markedly Impaired in Human Subcutaneous Tissue and Plasma," *Biosensors & Bioelectronics*, vol. 8, 1993, pp. 473-482.

Korf, J., et al., "Monitoring of Glucose and Lactate Using Microdialysis: Applications in Neonates and Rat Brain," *Developmental Neuroscience*, vol. 15, 1993, pp. 240-246.

Koudelka, M., et al., "In-Vivo Behaviour of Hypodermically Implanted Microfabricated Glucose Sensors", *Biosensors & Bioelectronics*, vol. 6, 1991, pp. 31-36.

Kulys, J., et al., "Mediatorless Peroxidase Electrode and Preparation of Bienzyme Sensors", *Bioelectrochemistry and Bioenergetics*, vol. 24, 1990, pp. 305-311.

Lager, W., et al., "Implantable Electrocatalytic Glucose Sensor", *Hormone Metabolic Research*, vol. 26, 1994, pp. 526-530.

Laurell, T., "A Continuous Glucose Monitoring System Based on Microdialysis", *Journal of Medical Engineering & Technology*, vol. 16, No. 5, 1992, pp. 187-193.

Lindner, E., et al., "Flexible (Kapton-Based) Microsensor Arrays of High Stability for Cardiovascular Applications", *Journal of the Chemical Society, Faraday Transactions*, vol. 89, No. 2, 1993, pp. 361-367.

Lortz, J., et al., "What is Bluetooth? We Explain The Newest Short-Range Connectivity Technology", *Smart Computing Learning Series, Wireless Computing*, vol. 8, Issue 5, 2002, pp. 72-74.

Maidan, R., et al., "Elimination of Electrooxidizable Interferant-Produced Currents in Amperometric Biosensors", *Analytical Chemistry*, vol. 64, No. 23, 1992, pp. 2889-2896.

Malin, S. F., et al., "Noninvasive Prediction of Glucose by Near-Infrared Diffuse Reflectance Spectoscopy", *Clinical Chemistry*, vol. 45, No. 9, 1999, pp. 1651-1658.

Marko-Varga, G., et al., "Enzyme-Based Biosensor as a Selective Detection Unit in Column Liquid Chromatography", *Journal of Chromatography A*, vol. 660, 1994, pp. 153-167.

Mastrototaro, J. J., et al., "An Electroenzymatic Glucose Sensor Fabricated on a Flexible Substrate", *Sensors and Actuators B*, vol. 5, 1991, pp. 139-144.

Mauras, N., et al., "Lack of Accuracy of Continuous Glucose Sensors in Healthy, Nondiabetic Children: Results of the Diabetes Research in Children Network (DirecNet) Accuracy Study," *Journal of Pediatrics*, 2004, pp. 770-775.

McGarraugh, G., et al., "Glucose Measurements Using Blood Extracted from the Forearm and the Finger", *TheraSense, Inc.*, 2001, 16 Pages.

McGarraugh, G., et al., "Physiological Influences on Off-Finger Glucose Testing", *Diabetes Technology & Therapeutics*, vol. 3, No. 3, 2001, pp. 367-376.

McKean, B. D., et al., "A Telemetry-Instrumentation System for Chronically Implanted Glucose and Oxygen Sensors", *IEEE Transactions on Biomedical Engineering*, vol. 35, No. 7, 1988, pp. 526-532.

McNeil, C. J., et al., "Thermostable Reduced Nicotinamide Adenine Dinucleotide Oxidase: Application to Amperometric Enzyme Assay", *Analytical Chemistry*, vol. 61, No. 1, 1989, pp. 25-29.

Miyawaki, O., et al., "Electrochemical and Glucose Oxidase Coenzyme Activity of Flavin Adenine Dinucleotide Covalently Attached to Glassy Carbon at the Adenine Amino Group", *Biochimica et Biophysica Acta*, vol. 838, 1985, pp. 60-68.

Moatti-Sirat, D., et al., "Evaluating in Vitro and in Vivo the Interference of Ascorbate and Acetaminophen on Glucose Detection by a Needle-Type Glucose Sensor", *Biosensors & Bioelectronics*, vol. 7, 1992, pp. 345-352.

Moatti-Sirat, D., et al., "Reduction of Acetaminophen Interference in Glucose Sensors by a Composite Nafion Membrane: Demonstration in Rats and Man", *Diabetologia*, vol. 37, 1994, pp. 610-616.

Moatti-Sirat, D., et al., "Towards Continuous Glucose Monitoring: in Vivo Evaluation of a Miniaturized Glucose Sensor Implanted for Several Days in Rat Subcutaneous Tissue", *Diabetologia*, vol. 35, 1992, pp. 224-330.

Nagy, G., et al., "A New Type of Enzyme Electrode: The Ascorbic Acid Eliminator Electrode", *Life Sciences*, vol. 31, No. 23, 1982, pp. 2611-2616.

Nakamura, S., et al., "Effect of Periodate Oxidation on the Structure and Properties of Glucose Oxidase", *Biochimica et Biophysica Acta.*, vol. 445, 1976, pp. 294-308.

Narasimham, K., et al., "p-Benzoquinone Activation of Metal Oxide Electrodes for Attachment of Enzymes", *Enzyme and Microbial Technology*, vol. 7, 1985, pp. 283-286.

Ohara, T. J., "Osmium Bipyridyl Redox Polymers Used in Enzyme Electrodes", *Platinum Metals Review*, vol. 39, No. 2, 1995, pp. 54-62.

Ohara, T. J., et al., "'Wired' Enzyme Electrodes for Amperometric Determination of Glucose or Lactate in the Presence of Interfering Substances", *Analytical Chemistry*, vol. 66, No. 15, 1994, pp. 2451-2457.

Ohara, T. J., et al., "Glucose Electrodes Based on Cross-Linked $[Os(bpy)_2Cl]^{+/2+}$ Complexed Poly(1-Vinylimidazole) Films", *Analytical Chemistry*, vol. 65, No. 23, 1993, pp. 3512-3517.

Olievier, C. N., et al., "In Vivo Measurement of Carbon Dioxide Tension with a Miniature Electrodes", *Pflugers Archiv: European Journal of Physiology*, vol. 373, 1978, pp. 269-272.

Paddock, R. M., et al., "Electrocatalytic Reduction of Hydrogen Peroxide via Direct Electron Transfer From Pyrolytic Graphite Electrodes to Irreversibly Adsorbed Cyctochrome C Peroxidase", *Journal of ElectroAnalytical Chemistry*, vol. 260, 1989, pp. 487-494.

Palleschi, G., et al., "A Study of Interferences in Glucose Measurements in Blood by Hydrogen Peroxide Based Glucose Probes", *Analytical Biochemistry*, vol. 159, 1986, pp. 114-121.

Pankratov, I., et al., "Sol-Gel Derived Renewable-Surface Biosensors", *Journal of ElectroAnalytical Chemistry*, vol. 393, 1995, pp. 35-41.

Pathak, C., et al., "Rapid Photopolymerization of Immunoprotective Gels in Contact with Cells and Tissue", *Journal of the American Chemical Society*, vol. 114, No. 21, 1992, pp. 8311-8312.

Pickup, J., "Developing Glucose Sensors for in Vivo Use", *Tibtech*, vol. 11, 1993, pp. 285-291.

Pickup, J., et al., "Implantable Glucose Sensors: Choosing the Appropriate Sensing Strategy", *Biosensors*, vol. 3, 1987/88, pp. 335-346.

Pickup, J., et al., "In Vivo Molecular Sensing in Diabetes Mellitus: An Implantable Glucose Sensor with Direct Electron Transfer", *Diabetologia*, vol. 32, 1989, pp. 213-217.

Pickup, J., et al., "Potentially-Implantable, Amperometric Glucose Sensors with Mediated Electron Transfer: Improving the Operating Stability", *Biosensors*, vol. 4, 1989, pp. 109-119.

Pishko, M. V., et al., "Amperometric Glucose Microelectrodes Prepared Through Immobilization of Glucose Oxidase in Redox Hydrogels", *Analytical Chemistry*, vol. 63, No. 20, 1991, pp. 2268-2272.

Poitout, V., et al., "A Glucose Monitoring System for on Line Estimation in Man of Blood Glucose Concentration Using a Miniaturized Glucose Sensor Implanted in the Subcutaneous Tissue and a Wearable Control Unit", *Diabetolgia*, vol. 36, 1993, pp. 658-663.

Poitout, V., et al., "Calibration in Dogs of a Subcutaneous Miniaturized Glucose Sensor Using a Glucose Meter for Blood Glucose Determination", *Biosensors & Bioelectronics*, vol. 7, 1992, pp. 587-592.

Poitout, V., et al., "In Vitro and in Vivo Evaluation in Dogs of a Miniaturized Glucose Sensor", *ASAIO Transactions*, vol. 37, No. 3, 1991, pp. M298-M300.

Pollak, A., et al., "Enzyme Immobilization by Condensation Copolymerization into Cross-Linked Polyacrylamide Gels", *Journal of the American Chemical Society*, vol. 102, No. 20, 1980, pp. 6324-6336.

Quinn, C. P., et al., "Kinetics of Glucose Delivery to Subcutaneous Tissue in Rats Measured with 0.3-mm Amperometric Microsensors", *The American Physiological Society*, 1995, E155-E161.

Reach, G., et al., "Can Continuous Glucose Monitoring Be Used for the Treatment of Diabetes?", *Analytical Chemistry*, vol. 64, No. 6, 1992, pp. 381-386.

Rebrin, K., et al., "Automated Feedback Control of Subcutaneous Glucose Concentration in Diabetic Dogs", *Diabetologia*, vol. 32, 1989, pp. 573-576.

Reusch, W., "Other Topics: Organometallic Chemistry: Organometallic Compounds: Main Group Organometallic Compounds," *Virtual Textbook of Organic Chemistry*, 1999, Rev. 2007, 25 pages.

Roe, J. N., et al., "Bloodless Glucose Measurements", *Critical Review in Therapeutic Drug Carrier Systems*, vol. 15, Issue 3, 1998, pp. 199-241.

Sacks (ED), "Guidelines and Recommendations for Laboratory Analysis in the Diagnosis and Management of Diabetes Mellitus," *The National Academy of Clinical Biochemistry Presents Laboratory Medicine Practice Guidelines*, vol. 13, 2002, pp. 8-11, 21-23, 52-56, 63.

Sakakida, M., et al., "Development of Ferrocene-Mediated Needle-Type Glucose Sensor as a Measure of True Subcutaneous Tissue Glucose Concentrations", *Artificial Organs Today*, vol. 2, No. 2, 1992, pp. 145-158.

Sakakida, M., et al., "Ferrocene-Mediated Needle-Type Glucose Sensor Covered with Newly Designed Biocompatible Membrane", *Sensors and Actuators B*, vol. 13-14, 1993, pp. 319-322.

Salehi, C., et al., "A Telemetry-Instrumentation System for Long-Term Implantable Glucose and Oxygen Sensors", *Analytical Letters*, vol. 29, No. 13, 1996, pp. 2289-2308.

Samuels, G. J., et al., "An Electrode-Supported Oxidation Catalyst Based on Ruthenium (IV). pH 'Encapsulation' in a Polymer Film", *Journal of the American Chemical Society*, vol. 103, No. 2, 1981, pp. 307-312.

Sasso, S. V., et al., "Electropolymerized 1,2-Diaminobenzene as a Means to Prevent Interferences and Fouling and to Stabilize Immobilized Enzyme in Electrochemical Biosensors", *Analytical Chemistry*, vol. 62, No. 11, 1990, pp. 1111-1117.

Scheller, F. W., et al., "Second Generation Biosensors," *Biosensors & Bioelectronics*, vol. 6, 1991, pp. 245-253.

Scheller, F., et al., "Enzyme Electrodes and Their Application", *Philosophical Transactions of The Royal Society of London B*, vol. 316, 1987, pp. 85-94.

Schmehl, R. H., et al., "The Effect of Redox Site Concentration on the Rate of Mediated Oxidation of Solution Substrates by a Redox Copolymer Film", *Journal of ElectroAnalytical Chemistry*, vol. 152, 1983, pp. 97-109.

Schmidt, F. J., et al., "Calibration of a Wearable Glucose Sensor", *The International Journal of Artificial Organs*, vol. 15, No. 1, 1992, pp. 55-61.

Schmidtke, D. W., et al., "Measurement and Modeling of the Transient Difference Between Blood and Subcutaneous Glucose Concentrations in the Rat After Injection of Insulin", *Proceedings of the National Academy of Sciences*, vol. 95, 1998, pp. 294-299.

Shaw, G. W., et al., "In Vitro Testing of a Simply Constructed, Highly Stable Glucose Sensor Suitable for Implantation in Diabetic Patients", *Biosensors & Bioelectronics*, vol. 6, 1991, pp. 401-406.

Shichiri, M., et al., "Glycaemic Control in Pancreatectomized Dogs with a Wearable Artificial Endocrine Pancreas", *Diabetologia*, vol. 24, 1983, pp. 179-184.

Shichiri, M., et al., "In Vivo Characteristics of Needle-Type Glucose Sensor—Measurements of Subcutaneous Glucose Concentrations in Human Volunteers", *Hormone and Metabolic Research Supplement Series*, vol. 20, 1988, pp. 17-20.

Shichiri, M., et al., "Membrane Design for Extending the Long-Life of an Implantable Glucose Sensor", *Diabetes Nutrition and Metabolism*, vol. 2, 1989, pp. 309-313.

Shichiri, M., et al., "Needle-type Glucose Sensor for Wearable Artificial Endocrine Pancreas", *Implantable Sensors for Closed-Loos Prosthetic Systems*, Chapter 15, 1985, pp. 197-210.

Shichiri, M., et al., "Telemetry Glucose Monitoring Device With Needle-Type Glucose Sensor: A Useful Tool for Blood Glucose Monitoring in Diabetic Individuals", *Diabetes Care*, vol. 9, No. 3, 1986, pp. 298-301.

Shichiri, M., et al., "Wearable Artificial Endocrine Pancreas With Needle-Type Glucose Sensor", *The Lancet*, 1982, pp. 1129-1131.

Shults, M. C., et al., "A Telemetry-Instrumentation System for Monitoring Multiple Subcutaneously Implanted Glucose Sensors", *IEEE Transactions on Biomedical Engineering*, vol. 41, No. 10, 1994, pp. 937-942.

Sittampalam, G., et al., "Surface-Modified Electrochemical Detector for Liquid Chromatography", *Analytical Chemistry*, vol. 55, No. 9, 1983, pp. 1608-1610.

Skoog, D. A., et al., "Evaluation of Analytical Data," *Fundamentals of Analytical Chemistry*, 1966, pp. 55.

Soegijoko, S., et al., "External Artificial Pancreas: A New Control Unit Using Microprocessor", *Hormone and Metabolic Research Supplement Series*, vol. 12, 1982, pp. 165-169.

Sprules, S. D., et al., "Evaluation of a New Disposable Screen-Printed Sensor Strip for the Measurement of NADH and Its Modification to Produce a Lactate Biosensor Employing Microliter Volumes", *Electroanalysis*, vol. 8, No. 6, 1996, pp. 539-543.

Sternberg, F., et al., "Calibration Problems of Subcutaneous Glucosensors when Applied 'In-Situ' in Man", *Hormone and Metabolic Research*, vol. 26, 1994, pp. 523-526.

Sternberg, R., et al., "Covalent Enzyme Coupling on Cellulose Acetate Membranes for Glucose Sensor Development", *Analytical Chemistry*, vol. 60, No. 24, 1988, pp. 2781-2786.

Sternberg, R., et al., "Study and Development of Multilayer Needle-Type Enzyme-Based Glucose Microsensors", *Biosensors*, vol. 4, 1988, pp. 27-40.

Suekane, M , "Immobilization of Glucose Isomerase", *Zettschrift fur Allgemeine Mikrobiologie*, vol. 22, No. 8, 1982, pp. 565-576.

Tajima, S., et al., "Simultaneous Determination of Glucose and 1,5-Anydroglucitol", *Chemical Abstracts*, vol. 111, No. 25, 1989, pp. 394.

Takamura, A., et al., Drug release from Poly(vinyl alcohol) Gel Prepared by Freeze-Thaw Procedure, *Journal of Controlled Release*, vol. 20, 1992, pp. 21-27.

Tarasevich, M. R., "Bioelectrocatalysis", *Comprehensive Treatise of Electrochemistry*, vol. 10, 1985, pp. 231-295.

Tatsuma, T., et al., "Enzyme Monolayer- and Bilayer-Modified Tin Oxide Electrodes for the Determination of Hydrogen Peroxide and Glucose", *Analytical Chemistry*, vol. 61, No. 21, 1989, pp. 2352-2355.

Taylor, C., et al., "'Wiring' of Glucose Oxidase Within a Hydrogel Made with Polyvinyl Imidazole Complexed with $[(Os-4,4"-dimethoxy-2,2"-bipyridine)Cl]^{+/2+}$", *Journal of ElectroAnalytical Chemistry*, vol. 396, 1995, pp. 511-515.

Thompson, M., et al., "In Vivo Probes: Problems and Perspectives", *Clinical Biochemistry*, vol. 19, 1986, pp. 255-261.

Travenol Laboratories, Inc., *An Introduction to "Eugly"*, Book 1, 1985, pp. 1-22.

Trojanowicz, M., et al., "Enzyme Entrapped Polypyrrole Modified Electrode for Flow-Injection Determination of Glucose", *Biosensors & Bioelectronics*, vol. 5, 1990, pp. 149-156.

Tsalikian, E., et al., "Accuracy of the GlucoWatch G2® Biographer and the Continuous Glucose Monitoring System During Hypoglycemia: Experience of the Diabetes Research in Children Network", *Diabetes Care*, vol. 27, No. 3, 2004, pp. 722-726.

Turner, A., et al., "Diabetes Mellitus: Biosensors for Research and Management", *Biosensors*, vol. 1, 1985, pp. 85-115.

Turner, R. F., et al., "A Biocompatible Enzyme Electrode for Continuous in vivo Glucose Monitoring in Whole Blood", *Sensors and Actuators B*, vol. 1, 1990, pp. 561-564.

Tuzhi, P., et al., "Constant Potential Pretreatment of Carbon Fiber Electrodes for in Vivo Electrochemistry", *Analytical Letters*, vol. 24, No. 6, 1991, pp. 935-945.

Umana, M., "Protein-Modified Electrochemically Active Biomaterial Surface", *U.S. Army Research Office, Analytical and Chemical Sciences Research Triangle Institute*, 1988, pp. 1-9.

Updike, S. J., et al., "Principles of Long-Term Fully Implanted Sensors with Emphasis on Radiotelemetric Monitoring of Blood Glucose from Inside a Subcutaneous Foreign Body Capsule (FBC)", *Biosensors in the Body: Continuous in vivo Monitoring*, Chapter 4, 1997, pp. 117-137.

Urban, G., et al., "Miniaturized Thin-Film Biosensors Using Covalently Immobilized Glucose Oxidase", *Biosensors & Bioelectronics*, vol. 6, 1991, pp. 555-562.

Velho, G., et al., "In Vitro and in Vivo Stability of Electrode Potentials in Needle-Type Glucose Sensors", *Diabetes*, vol. 38, No. 2, 1989, pp. 164-171.

Velho, G., et al., "Strategies for Calibrating a Subcutaneous Glucose Sensor", *Biomedica Biochimica Acta*, vol. 48, 1989, pp. 957-964.

Von Woedtke, T., et al., "In Situ Calibration of Implanted Electrochemical Glucose Sensors", *Biomedica Biochimica Acta*, vol. 48, 1989, pp. 943-952.

Vreeke, M. S., et al., "Hydrogen Peroxide Electrodes Based on Electrical Connection of Redox Centers of Various Peroxidases to Electrodes through a Three-Dimensional Electron-Relaying Polymer Network", *Diagnostic Biosensors Polymers*, Chapter 15, 1993, pp. 180-193.

Vreeke, M., et al., "Hydrogen Peroxide and β-Nicotinamide Adenine Dinucleotide Sensing Amperometric Electrodes Based on Electrical Connection of Horseradish Peroxidase Redox Centers to Electrodes through a Three-Dimensional Electron Relaying Polymer Network", *Analytical Chemistry*, vol. 64 No. 24, 1992, pp. 3084-3090.

Wang, D. L., et al., "Miniaturized Flexible Amperometric Lactate Probe", *Analytical Chemistry*, vol. 65, No. 8, 1993, pp. 1069-1073.

Wang, J., et al., "Activation of Glassy Carbon Electrodes by Alternating Current Electrochemical Treatment", *Analytica Chimica Acta*, vol. 167, 1985, pp. 325-334.

Wang, J., et al., "Amperometric Biosensing of Organic Peroxides with Peroxidase-Modified Electrodes", *Analytica Chimica Acta*, vol. 254, 1991, pp. 81-88.

Wang, J., et al., "Screen-Printable Sol-Gel Enzyme-Containing Carbon Inks", *Analytical Chemistry*, vol. 68, No. 15, 1996, pp. 2705-2708.

Wang, J., et al., "Sol-Gel-Derived Metal-Dispersed Carbon Composite Amperometric Biosensors", *Electroanalysis*, vol. 9, No. 1, 1997, pp. 52-55.

Williams, D. L., et al., "Electrochemical-Enzymatic Analysis of Blood Glucose and Lactate", *Analytical Chemistry*, vol. 42, No. 1, 1970, pp. 118-121.

Wilson, G. S., et al., "Progress Toward the Development of an Implantable Sensor for Glucose", *Clinical Chemistry*, vol. 38, No. 9, 1992, pp. 1613-1617.

Yabuki, S., et al., "Electro-Conductive Enzyme Membrane", *Journal of the Chemical Society, Chemical Communications*, 1989, pp. 945-946.

Yang, C., et al., "A Comparison of Physical Properties and Fuel Cell Performance of Nafion and Zirconium Phosphate/Nafion Composite Membranes," *Journal of Membrane Science*, vol. 237, 2004, pp. 145-161.

Yang, L., et al., "Determination of Oxidase Enzyme Substrates Using Cross-Flow Thin-Layer Amperometry", *Electroanalysis*, vol. 8, No. 8-9, 1996, pp. 716-721.

Yao, S. J., et al., "The Interference of Ascorbate and Urea in Low-Potential Electrochemical Glucose Sensing", *Proceedings of the Twelfth Annual International Conference of the IEEE Engineering in Medicine and Biology Society*, vol. 12, Part 2, 1990, pp. 487-489.

Yao, T., "A Chemically-Modified Enzyme Membrane Electrode as an Amperometric Glucose Sensor", *Analytica Chimica Acta*, vol. 148, 1983, pp. 27-33.

Ye, L., et al., "High Current Density 'Wired' Quinoprotein Glucose Dehydrogenase Electrode", *Analytical Chemistry*, vol. 65, No. 3, 1993, pp. 238-241.

Yildiz, A., et al., "Evaluation of an Improved Thin-Layer Electrode", *Analytical Chemistry*, vol. 40, No. 7, 1968, pp. 1018-1024.

Zamzow, K., et al., "New Wearable Continuous Blood Glucose Monitor (BGM) and Artificial Pancreas (AP)", *Diabetes*, vol. 39, 1990, pp. 5A-20.

Zhang, Y., et al., "Application of Cell Culture Toxicity Tests to the Development of Implantable Biosensors", *Biosensors & Bioelectronics*, vol. 6, 1991, pp. 653-661.

Zhang, Y., et al., "Elimination of the Acetaminophen Interference in an Implantable Glucose Sensor", *Analytical Chemistry*, vol. 66, No. 7, 1994, pp. 1183-1188.

U.S. Appl. No. 12/426,887, Office Action mailed Jul. 21, 2011.
U.S. Appl. No. 12/426,918, Office Action mailed Mar. 18, 2011.

\* cited by examiner

GLUCOSE MEASURING DEVICE FOR USE IN PERSONAL AREA NETWORK

RELATED APPLICATION

This application claims priority under 35 USC §119 to Provisional Patent Application No. 60/477,730 filed on Jun. 10, 2003, entitled "Glucose Measuring Device For Use In Personal Area Network", the disclosure of which is incorporated herein by reference for all purposes.

FIELD OF THE INVENTION

This invention relates to a device and method for determining and reporting glucose readings in wireless personal area networks for diabetics.

BACKGROUND

The number of diagnosed cases of diabetes continues to increase in the U.S. and throughout the world, creating enormous economic and public health consequences. Devices and therapies that improve the quality of life for the diabetic patient thus are important not only for the patient, but for society at large. One area in which recently developed technologies have been able to improve the standard of care has been in the maintenance of tight control over the blood glucose levels. It is well known that if a diabetic patient's blood glucose values can be maintained in a relatively narrow and normal range of from about 80 milligrams per deciliter (mg/dL) to about 120 mg/dL, the physiologically damaging consequences of unchecked diabetes can be minimized. With better blood glucose information, diabetic patients can better exercise tight control of their blood glucose level through a variety of means, including diet, exercise, and medication. For this reason a large industry has developed to provide the diabetic population with ever more convenient and accurate ways to measure blood glucose. There are many forms of these measuring devices; one common type is represented by hand-held electronic meters which receive blood samples via enzyme-based "test strips". In using these systems, the patient lances a finger or alternate body site to obtain a blood sample, the strip is inserted into a test strip opening in the meter housing, the sample is applied to the test strip and the electronics in the meter convert a current generated by the enzymatic reaction in the test strip to a blood glucose value. The result is displayed on the (typically) liquid crystal display of the meter. Usually, this display must be large so that diabetics who often have deteriorating vision, can more easily see the result.

It is known that such hand-held meters can advantageously be manufactured to include wireless communication capability. Such capability can assist the user in downloading data to a home computer or to a handheld computing device, for example. This minimizes the need for the user to write down data and transfer it later to an electronic record.

It is also known that hand-held meters are often given to users, so that suppliers of the strips used with the meters can generate greater strip sales. This makes the cost of the hand-held meters critical to profitability of the manufacturers. If the cost of a meter is relatively high, profits from the sale of strips will be small or worse yet, non-existent. If the cost of the meter can be reduced, profitability is improved.

Lastly, it is well known that if a strip and meter system is convenient to use, patients will test more often and compliance with treatment programs will improve. Including wireless communication in the meter adds convenience, but at a cost. For these reasons, there is a continuing need for a low cost meter and strip glucose monitoring system that nevertheless has highly convenient features, including wireless communication capabilities.

SUMMARY OF THE INVENTION

The present invention is a glucose monitoring system which includes a glucose meter system of the meter and strip type that includes wireless communication capabilities. The system can be a reduced cost system however, by eliminating components from the meter, such as the relatively large LCD display, and instead relying on such components in other electronic devices that now typically surround a patient almost every day and can form part of the monitoring system. By eliminating high cost components from the meter but retaining the wireless communication functionality, the meter portion of the system can be relatively low cost, yet the system overall provides highly convenient features to the user.

Accordingly, in one embodiment of the present invention, there is provided a data communication system including a data network, a client unit operatively coupled to the data network, and a server unit operatively coupled to the data network for communicating with the client unit, said server unit further configured to receive blood glucose related data from the client unit over the data network.

The client unit may be configured to encrypt the blood glucose related data for wireless transmission over the data network to the server unit. Moreover, the client unit may include a blood glucose meter.

In an alternate embodiment, the data communication over the data network may include one of a 802.11 protocol, a Bluetooth® protocol, a radio frequency (RF) protocol, and an Infrared Data Association® (IrDA®) protocol.

Furthermore, the server unit may in one embodiment include a display.

The system in accordance with yet another embodiment may include a base unit configured to communicate with the server unit over the data network, the base unit configured to store data received from the server unit, and further, the base unit configured to provide an insulin pump protocol to said server unit.

The data network may include a personal area network, where the personal area network is configured for short range wireless communication.

In a further embodiment, the client unit may be configured with password protection.

Additionally, the client unit may include one or more of a compact handheld device, a personal digital assistant, and a mobile telephone.

In accordance with another embodiment of the present invention, there is provided a method of providing a data communication system including the steps of establishing a data network, operatively coupling a client unit to the data network, and operatively coupling a server unit to the data network to communicate with the client unit, the server unit further configured to receive blood glucose related data from the client unit over the data network.

The method may further include the step of encrypting the blood glucose related data for wireless transmission over the data network.

Moreover, the step of establishing the data network may include the step of implementing one of a 802.11 protocol, a Bluetooth® protocol, an RF protocol, and an IrDA® protocol.

Also, the method in a further embodiment may include the step of displaying the data received from the client unit.

Moreover, in another embodiment, the method may include the step of configuring a base unit to communicate with the server unit over the data network, the step further including storing data received from the server unit. Also, the step of configuring the base unit further may include the step of providing an insulin pump protocol to said server unit. Moreover, the method may also include configuring the personal area network for short range wireless communication.

Additionally, the method may include the step of password protecting access to the client unit.

In accordance with yet another embodiment of the present invention, there is provided a personal area network, a blood glucose meter operatively coupled to the personal area network, and a server unit operatively coupled to the personal area network for wirelessly communicating with the meter, said server unit further configured to receive blood glucose data from the meter over the personal area network.

The invention will now be described by reference to the figures, wherein like reference numerals and names indicate corresponding structure throughout the several views.

DETAILED DESCRIPTION

Figure 1:
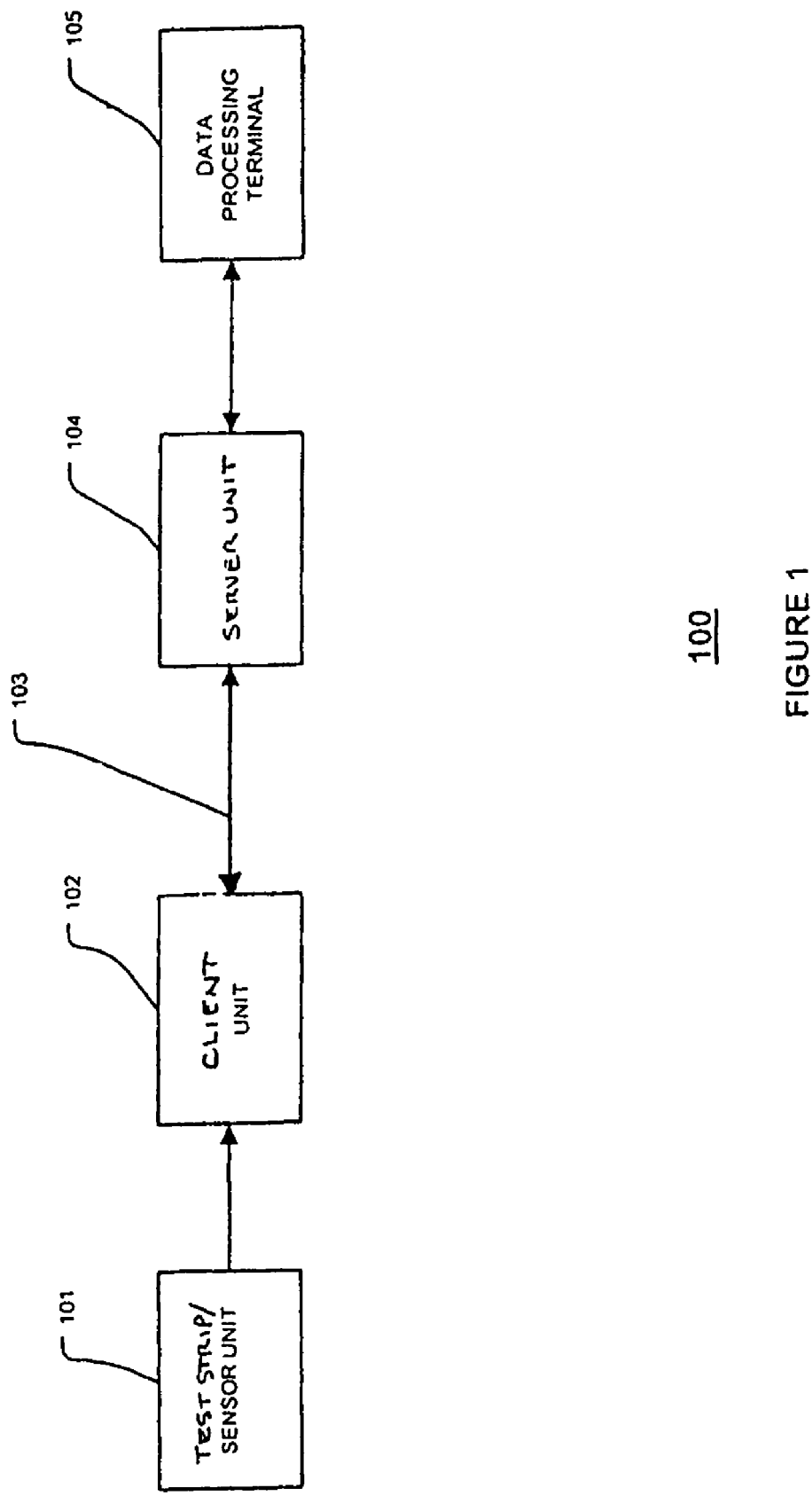
FIG. 1 is a schematic view showing typical data signal flow between devices of a wireless system constructed according to one embodiment of the present invention.

Referring to FIG. 1, a wireless system constructed according to a preferred embodiment of the present invention will be described. Test strip 101 electrically communicates with client device 102, which wirelessly communicates with server device 104, such as by two-way radio frequency (RF) contact, infrared (IR) contact, Bluetooth® contact or other known wireless means 103. Optionally, server device 104 can also communicate with other devices such as data processing terminal 105 by direct electronic contact, via RF, IR, Bluetooth® or other wireless means.

Figure 4:
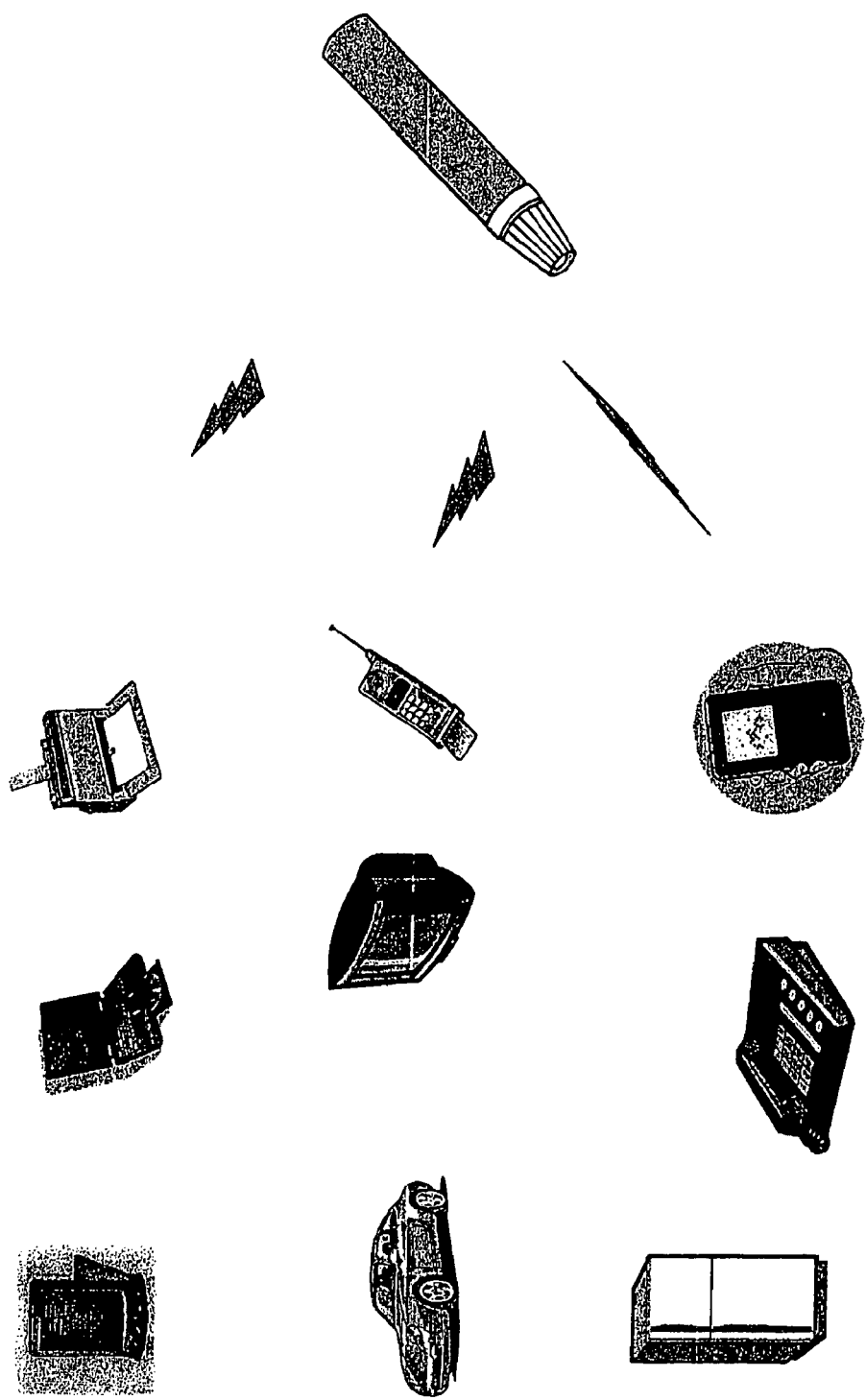
FIG. 4 is a pictoral view showing a typical client device and typical server devices.

Test strip 101 is a commonly known electrochemical analyte test strip, such as a blood glucose test strip as described in U.S. patent application Ser. No. 09/434,026 filed Nov. 4, 1999 entitled "Small Volume In Vitro Analyte Sensor and Methods", incorporated herein by reference. It is mechanically received in a test strip port of a client device 102, similar to a commonly known hand-held blood glucose meter as described in the aforementioned patent application. In the preferred embodiment, client device 102 is constructed without a user interface or display to keep the size and cost of device 102 to a minimum. Client device 102 can take the form of a highlighter or easel-sized pen, as shown in FIG. 4, and can be powered by a single AA or AAA size battery.

Client device 102 wirelessly communicates with server device 104, preferably using a common standard such as 802.11 or Bluetooth® wireless protocol, or an IrDA® infrared protocol. Server device 104 can be another portable device, such as a Personal Digital Assistant (PDA) or notebook computer, or a larger device such as a desktop computer, appliance, etc. as shown by the examples in FIG. 4. Preferably, server device 104 does have a display, such as a liquid crystal display (LCD), as well as an input device, such as buttons, a keyboard, mouse or touch-screen. With this arrangement, the user can control client device 102 indirectly by interacting with the user interface(s) of server device 104, which in turn interacts with client device 102 across wireless link 103.

Server device 104 can also communicate with another device 105, such as for sending glucose data from devices 102 and 104 to data storage in device 105, and/or receiving instructions or an insulin pump protocol from a health care provider computer 105. Examples of such communication include a PDA 104 synching data with a personal computer (PC) 105, a mobile phone 104 communicating over a cellular network with a computer 105 at the other end, or a household appliance 104 communicating with a computer system 105 at a physician's office.

Figure 2:
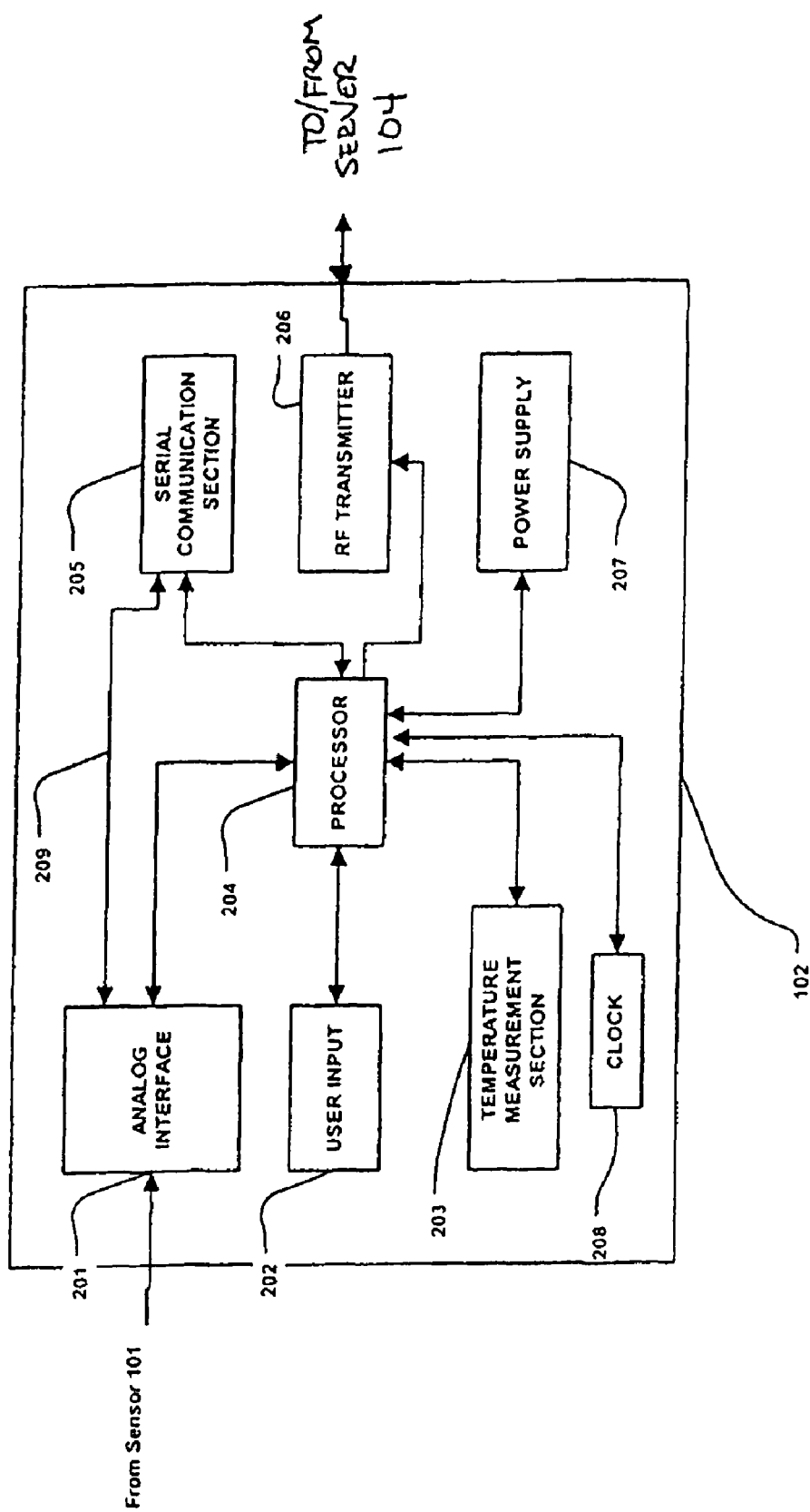
FIG. 2 is a schematic view showing the client device of FIG. 1.

Referring to FIG. 2, internal components of the client device 102 such a blood glucose meter of the preferred embodiment are shown. As shown, the client device 102 includes an analog interface 201 configured to communicate with the test strip 101 (FIG. 1), a user input 202, and a temperature detection section 203, each of which is operatively coupled to a processor 204 such as a central processing unit (CPU). Further shown in FIG. 2 are a serial communication section 205 and an RF transmitter 206, each of which is also operatively coupled to the client device processor 204. Moreover, a power supply 207 is also provided in the client device 102 to provide the necessary power for the client device 102. Additionally, as can be seen from the Figure, a clock 208 is provided to, among others, supply real time information to the client device processor 204.

Alternatively, user input 202, such as push button(s), and other sections can be eliminated to reduce size and cost of client device 102. The glucose meter housing may contain any glucose sensing system of the type well known in the art that can be configured to fit into a small profile. Such a system can include, for example, the electrochemical glucose strip and meter sensing system sold by Abbott Diabetes Care Inc. of Alameda, Calif. under the FreeStyle® brand, or other strip and meter glucose measuring systems. The housing may thus encompass the sensor electronics and a strip connector, which connector is accessed via a test strip port opening in the housing. The housing will typically also include a battery or batteries.

Figure 3:
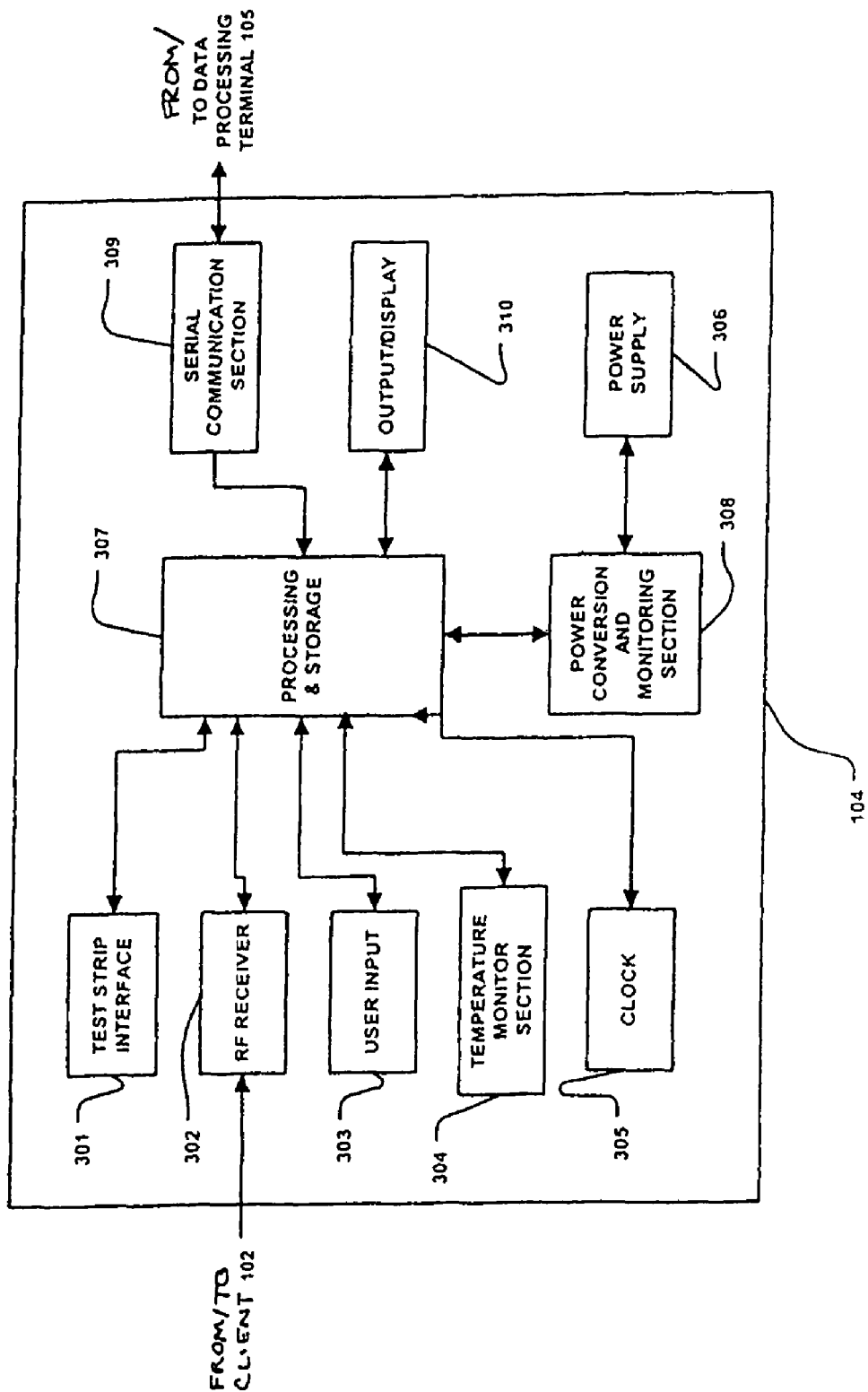
FIG. 3 is a schematic view showing the server device of FIG. 1.

Referring to FIG. 3, internal components of a server device 104 of the preferred embodiment are shown. Referring to FIG. 3, the server device 104 includes a blood glucose test strip interface 301, an RF receiver 302, an input unit 303, a temperature detection section 304, and a clock 305, each of which is operatively coupled to a server device processor 307. As can be further seen from the Figure, the server device 104 also includes a power supply 306 operatively coupled to a power conversion and monitoring section 308. Further, the power conversion and monitoring section 308 is also coupled to the server device processor 307. Moreover, also shown are a receiver serial communication section 309, and an output 310, each operatively coupled to the server device processor 307.

Note that a redundant test strip interface 301 can be provided if desired for receiving test strips 101 (FIG. 1). Device 104 can be a proprietary unit designed specifically for use with blood glucose meters, or can be a generic, multipurpose device such as a standard PDA. An example of a similar device designed for blood glucose testing is disclosed in U.S. Pat. No. 6,560,471 issued May 6, 2003 to Abbott Diabetes Care Inc. entitled "Analyte Monitoring Device and Methods of Use", incorporated herein by reference.

FIG. 4 shows examples of the devices to and from which the meter of the invention can communicate. Such devices will become part of an individual's personal area network and each becomes enabled with short range wireless communication capabilities. Desktop, laptop and handheld computers, as well as printers can be so enabled and will provide displays and printouts valuable as records for the diabetic. Telephones will also be enabled in this fashion and can be used for displaying glucose data as well as further transmitting the data over larger networks. Many of these devices can assist the diabetic by responding to glucose levels by providing alarms, or suggesting that action be taken to correct a hypo or hyperglycemic condition, or to call necessary medical assistance. Diabetics are aware of the risks involved in driving when glucose levels are out of range and particularly when they are too low. Thus, the navigation computer in the diabetic's car may become part of the local area network and will download glucose data from the meter when the diabetic enters the car. For safety sake, the car computer system may be programmed to require that the diabetic perform a glucose test before driving, and more specifically the car may be disabled unless the diabetic takes the test and the result is in an appropriate range.

The pen shaped client device 102 shown in FIG. 4 preferably has a test strip port 201 (not shown in FIG. 4) located on its distal end. Because the sensitive analog "front end" circuitry associated with measuring the very small electrochemistry currents from test strips 101 is located adjacent strip port 201, it is advisable to not design a wireless link antenna too close to this distal end as it may interfere with the proper operation of the glucose sensing circuitry. On the other hand, if the wireless link antenna is located at the proximal end of the client device 102, it will likely be covered by the hand of the user holding it, which may limit the range of the low transmission power device to an unacceptable distance. Accordingly, it is preferable to design the layout of client device 102 such that an internal antenna is located in a middle section of the device away from the distal and proximal ends.

Figure 5:
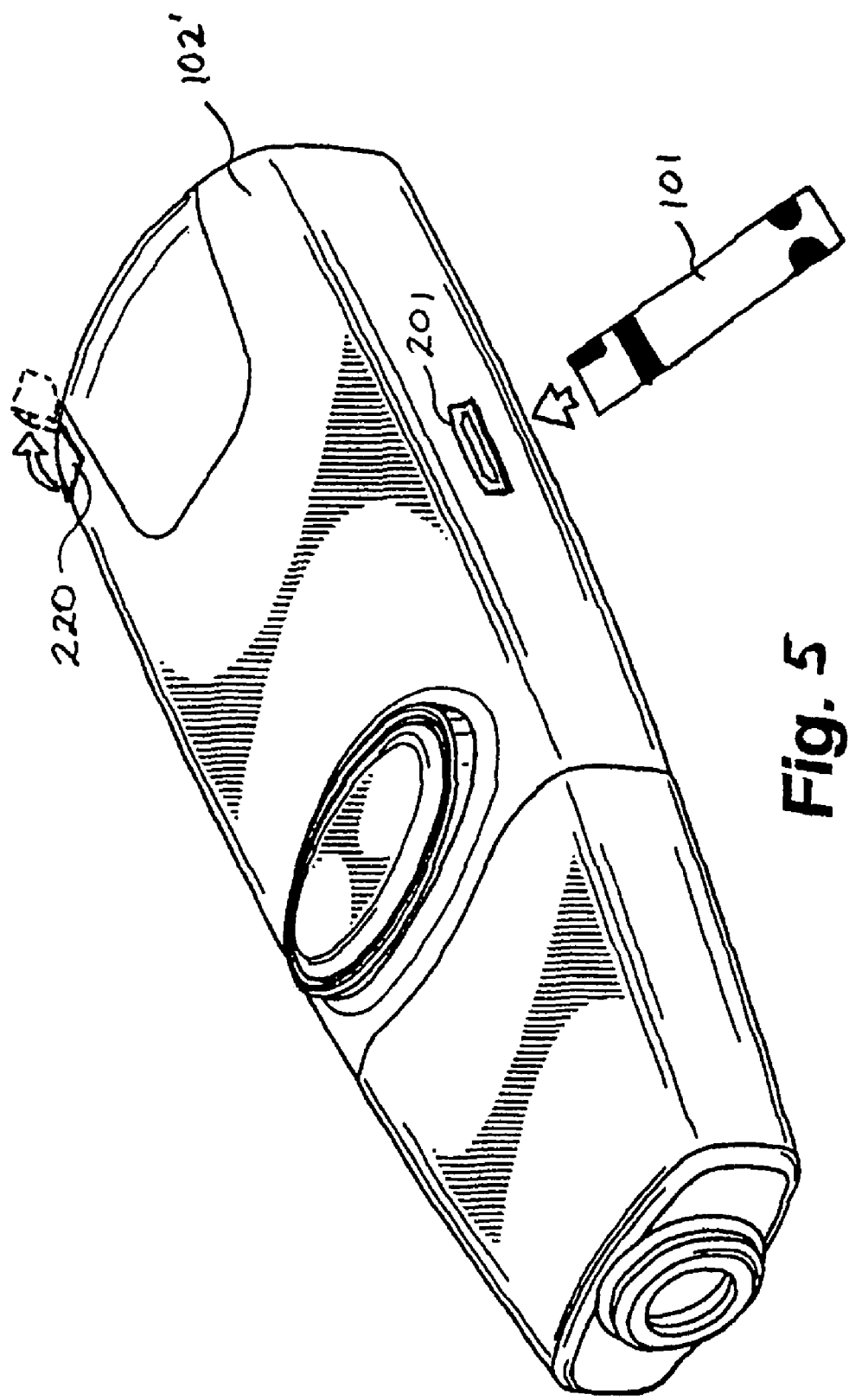
FIG. 5 is a perspective view showing an integrated device of an alternative embodiment.

Referring to FIG. 5, an alternative embodiment of the present invention is shown. Due to the reduced size of a blood glucose meter 102 when it does not include a display or push buttons, it can be combined with a lancing device to form an integrated unit 102'. Test strip port 201 can be located in the side of integrated device 102' or wherever there is room available. A test strip storage compartment can also be located within integrated device 102' and accessed through a flip-lid 220 or other suitable closure means. If room permits, a second test strip storage compartment (not shown) can be included so that fresh strips and used strips can be separately stored. Preferably, a desiccant is provided in one of the storage compartments to preserve the fresh strips. The design and use of lancing devices is described in U.S. Pat. No. 6,283,982 issued to TheraSense, Inc. on Sep. 4, 2001 entitled "Lancing Device and Method of Sample Collection", incorporated herein by reference. By integrating these features together in a single device without a user interface, the typical test kit that is carried around by people with diabetes can be made much smaller, easier to handle, and less costly.

Thus, one of the important features of the invention is reliance of the "displayless" glucose meter unit on a separate display device in order to minimize the complexity and cost of the meter unit. This permits the user to use the larger display units within his or her personal area network, all of which can be synchronized as they interact and communicate with the wireless enabled meter. When the meter is used, the sequences through which the user must "step" to complete the test are readily viewed on the larger display units (e.g. entering the calibration code, prompting application of the sample). At the same time the meter unit is simplified, smaller and less expensive to manufacture. Additionally, control buttons that are found on typical glucose meters can be eliminated, saving additional size and cost, since the user can rely on the user in out features of the server device instead. It is expected that the simplified, wireless enabled meters of the invention may ultimately become inexpensive enough to make them disposable after a specified number of uses, permitting the producer to routinely upgrade as appropriate.

Additionally, the system permits the user to include security coding at any time the meter unit accesses a display device, so that the user's data is secure. That is, it is considered an important feature of the invention that when the "client" meter of the invention is used, that the system will require the user to enter an identity code in order to verify that the person handling the meter is indeed an authorized user. Of course, it is possible for the system to permit more than one user if the meter owner so desires. Moreover, the user's data may optionally be encrypted prior to wireless transmission and thereafter respectively decrypted upon wireless reception.

While the module need not include a large or expensive display, it may nevertheless be advantageous to include some ability to advise the user of a glucose level which is determined when the module is used as a "stand-alone" unit. For example, the module could include a very low cost, small three digit LCD display. Alternatively, the module could include LED indicator lights (e.g. red for out of desired range, green for within desired range). Other possibilities include a red LED for below range, a green LED for within range, and a yellow LED for above range, or a column of LEDs or an electroluminescent strip (similar to those used on common batteries to indicate battery life) to indicate approximate or relative glucose levels.

Various other modifications and alterations in the structure and method of operation of this invention will be apparent to those skilled in the art without departing from the scope and spirit of the invention. Although the invention has been described in connection with specific preferred embodiments, it should be understood that the invention as claimed should not be unduly limited to such specific embodiments. It is intended that the following claims define the scope of the present invention and that structures and methods within the scope of these claims and their equivalents be covered thereby.

What is claimed is:

1. A data communication system, comprising:
    a data network; and
    a client unit comprising a housing and a wireless communication module, the client unit operatively coupled to the data network via the wireless communication module, the client unit including a glucose sensor in contact with a bodily fluid of a user, the bodily fluid comprising one of blood or interstitial fluid, wherein the wireless communication module transmits glucose related data to a computer system of a vehicle, wherein the vehicle computer system is programmed to disable the operation of the vehicle when the received glucose related data indicates a glucose value outside a predetermined range.

2. The system of claim 1 wherein the client unit encrypts the glucose related data to wirelessly transmit over the data network.

3. The system of claim 1 wherein the client unit includes a blood glucose meter having a strip port to receive a glucose test strip.

4. The system of claim 1 wherein the data communication over the data network includes one of a 802.11 protocol, a short range radio frequency (RF) protocol, an RF protocol, and an Infrared Data Association (IrDA) protocol.

5. The system of claim 1 wherein the vehicle includes a display.

6. The system of claim 1 further including a base unit to communicate with the client unit over the data network, to store data received from the client unit, and/or to provide an insulin dose information.

7. The system of claim 1 wherein the data network includes a personal area network.

8. The system of claim 7 wherein said personal area network provides short range wireless communication.

9. The system of claim 7 wherein the client unit is password protected.

10. The system of claim 1 wherein the client unit includes a displayless blood glucose meter.

11. A method, comprising:
establishing a data network to provide communication between a client unit and a computer system of a vehicle, the client unit including a glucose sensor in contact with a bodily fluid of a user, the bodily fluid comprising one of blood or interstitial fluid;
measuring glucose related data using the glucose sensor;
transmitting glucose related data received at the client unit over the data network to the computer system of the vehicle; and
disabling the operation of the vehicle when the received glucose related data indicates a glucose value outside a predetermined range.

12. The method of claim 11 further including encrypting the glucose related data for wireless transmission over the data network.

13. The method of claim 11 wherein establishing the data network includes the step of implementing one of a 802.11 protocol, a short range radio frequency (RF) protocol, an RF protocol, and an Infrared Data Association (IrDA) protocol.

14. The method of claim 11 further including displaying the data received from the client unit.

15. The method of claim 11 further including configuring a base unit to communicate with the client unit over the data network and storing data received from the client unit.

16. The method of claim 15 wherein configuring the base unit further includes providing an insulin dose information.

17. The method of claim 11 wherein the data network includes a personal area network.

18. The method of claim 17 further including configuring the personal area network for short range wireless communication.

19. The method of claim 17 further including password protecting access to the client unit.

20. A data communication system, comprising:
a personal area network;
a blood glucose meter including a housing, the meter operatively coupled to the personal area network, the blood glucose meter including a strip port coupled to the housing to receive a test strip, the blood glucose meter generating a blood glucose related data based on information from the test strip, and wirelessly transmitting the blood glucose related data via the personal area network; and
a vehicle computer system operatively coupled to the personal area network to wirelessly communicate with the meter and to receive blood glucose related data from the meter over the personal area network, the vehicle computer system including programming to disable the vehicle until after determining that the received blood glucose related data is within a predetermined range.

21. The system of claim 1 wherein the vehicle computer system is programmed to disable the vehicle until after determining that the received glucose related data is within a predetermined range.

22. The system of claim 1 wherein the vehicle computer system is programmed to require a glucose test from a client unit before a user can operate the vehicle.

23. The system of claim 1 wherein the vehicle computer system includes an integrated navigation system.

24. The system of claim 1 wherein the vehicle computer system outputs the received glucose related data.

25. The system of claim 24 wherein the received glucose related data is output using one or more of a visual indicator, an audible indicator, a vibratory indicator or one or more combinations thereof.

26. The system of claim 1 wherein the client unit does not include a display unit.

27. The system of claim 1 wherein the client unit includes a compartment to store a plurality of test strips.

28. The system of claim 27 wherein the housing of the client unit further includes a removable cover provided over the compartment.

29. The system of claim 6 wherein the base unit includes one or more of a laptop computer, a personal digital assistant, a telephone, or an electronic device.

30. The method of claim 11 wherein disabling the operation of the vehicle includes disabling the vehicle until a glucose test result is determined to be within a predetermined range.

31. The method of claim 30 including prompting a user to provide the glucose test result prior to operation of the vehicle.

32. The method of claim 30 including receiving the glucose test result from the client unit.

33. The method of claim 32 wherein the glucose test result is received over the data network.

34. The method of claim 11 further including outputting the received glucose related data.

35. The method of claim 34 wherein outputting the received glucose related data includes displaying the received glucose related data on a visual display of the vehicle.

36. The system of claim 1, wherein the vehicle computer system is further programmed to download the glucose related data from the client unit when a driver enters the vehicle.

37. The system of claim 1, wherein the predetermined range includes glucose levels above a hypoglycemic level and below a hyperglycemic level.

38. The method of claim 11, further comprising downloading the glucose related data from the client unit to the computer system of the vehicle when a driver enters the vehicle.

39. The system of claim 11, wherein the predetermined range includes glucose levels above a hypoglycemic level and below a hyperglycemic level.

40. The system of claim 20, wherein the vehicle computer system is further programmed to download the blood glucose related data from the blood glucose meter when the driver enters the vehicle.

41. The system of claim 20, wherein the predetermined range includes glucose levels above a hypoglycemic level and below a hyperglycemic level.

* * * * *